US010780137B2

(12) United States Patent
O'Doherty et al.

(10) Patent No.: US 10,780,137 B2
(45) Date of Patent: Sep. 22, 2020

(54) COMPOSITION TO IMPROVE GUT HEALTH AND ANIMAL PERFORMANCE AND METHODS OF MAKING THE SAME

(71) Applicant: BioAtlantis Limited, Tralee (IE)

(72) Inventors: John O'Doherty, Belfield (IE); John T. O'Sullivan, Tralee (IE)

(73) Assignee: Bioatlantis Limited, Tralee (IE)

( * ) Notice: Subject to any disclaimer, the term of this patent is extended or adjusted under 35 U.S.C. 154(b) by 0 days.

(21) Appl. No.: 16/505,348

(22) Filed: Jul. 8, 2019

(65) Prior Publication Data

US 2019/0343905 A1 Nov. 14, 2019

Related U.S. Application Data

(63) Continuation of application No. 15/905,361, filed on Feb. 26, 2018, which is a continuation of application No. 12/094,383, filed as application No. PCT/IE2006/000131 on Nov. 21, 2006, now abandoned.

(30) Foreign Application Priority Data

Nov. 21, 2005 (IE) .................................. S2005/0772

(51) Int. Cl.
*A61K 36/02* (2006.01)
*A61K 36/03* (2006.01)

(52) U.S. Cl.
CPC .............. *A61K 36/02* (2013.01); *A61K 36/03* (2013.01); *Y02A 50/473* (2018.01); *Y02A 50/481* (2018.01)

(58) Field of Classification Search
CPC ................................ A61K 36/02; A61K 36/03
See application file for complete search history.

(56) References Cited

U.S. PATENT DOCUMENTS

| | | | |
|---|---|---|---|
| 4,739,046 A | 4/1988 | Luzio | |
| 4,761,042 A | 8/1988 | Seibert et al. | |
| 4,891,220 A | 1/1990 | Donzis | |
| 5,591,428 A | 1/1997 | Bengmark et al. | |
| 5,622,939 A | 4/1997 | Jamas et al. | |
| 5,633,369 A | 5/1997 | Jamas et al. | |
| 5,705,184 A | 1/1998 | Donzis | |
| 5,948,405 A | 9/1999 | Cedro et al. | |
| 6,143,731 A | 11/2000 | Jamas et al. | |
| 6,214,337 B1 | 4/2001 | Hayen et al. | |
| 6,241,983 B1 | 6/2001 | Paul et al. | |
| 6,270,812 B1 | 8/2001 | Allen et al. | |
| 6,312,709 B1 | 11/2001 | Allen et al. | |
| 6,338,856 B1 | 1/2002 | Allen et al. | |
| 6,342,242 B1 | 1/2002 | Allen et al. | |
| 6,383,538 B1 | 5/2002 | Allen et al. | |
| 6,391,331 B1 | 5/2002 | Allen et al. | |
| 6,432,443 B1 | 8/2002 | Allen et al. | |
| 6,573,250 B2 | 6/2003 | Umeda et al. | |
| 6,841,181 B2 | 1/2005 | Jager et al. | |
| 6,939,864 B1 | 9/2005 | Johnson et al. | |
| 2001/0016220 A1 | 8/2001 | Jager et al. | |
| 2002/0022049 A1 | 2/2002 | Allen et al. | |
| 2002/0032170 A1 | 3/2002 | Jamas et al. | |
| 2002/0143174 A1 | 10/2002 | Patchen et al. | |
| 2002/0146484 A1 | 10/2002 | Fidler et al. | |
| 2003/0003134 A1 | 1/2003 | Allen et al. | |
| 2003/0039723 A1 | 2/2003 | Park | |
| 2003/0113306 A1* | 6/2003 | Collins | C12N 1/20 424/93.45 |
| 2003/0119780 A1 | 6/2003 | Yvin et al. | |
| 2003/0124170 A1 | 7/2003 | Gallaher et al. | |
| 2004/0058889 A1 | 3/2004 | Sorgente et al. | |
| 2004/0082539 A1 | 4/2004 | Kelly | |
| 2004/0138172 A1 | 7/2004 | Murata et al. | |
| 2004/0253253 A1 | 12/2004 | Cheung | |
| 2005/0020490 A1 | 1/2005 | Courie, Jr. et al. | |
| 2005/0058671 A1 | 3/2005 | Bedding et al. | |
| 2005/0118326 A1 | 6/2005 | Anfinsen et al. | |

FOREIGN PATENT DOCUMENTS

| | | |
|---|---|---|
| DE | 20 2005 000192 U1 | 3/2005 |
| EP | 0916269 A1 | 5/1999 |
| WO | 03/045414 A2 | 6/2003 |
| WO | 2006/088923 A | 8/2006 |
| WO | 2006/102108 A | 9/2006 |
| WO | 2006/123059 A | 11/2006 |
| WO | 2007/057873 A3 | 5/2007 |

OTHER PUBLICATIONS

Database WPI week 200377 Derwent Publishing ltd. London GB; AN 2003-818282 XP002450190 & JP 2003 146888A (Yakult Honsha KK) May 21, 2003.
Database WPI week 200325Derwent Publishing ltd. London GB; AN 2003-250820 XP002450190& JP 2002 223727 A (Rivertape Seiyaku KK) Aug. 13, 2002.
Goodridge, H.S., et al., Activation of the innate immune receptor Dectin-1 upon formation of a 'phagocytic synapse', Nature, Apr. 28, 2011, pp. 471-475.
International Search Report & Witten Opinion of the EPO for PCT/IE2006/000131 dated Sep. 25, 2007, 14 pp.
McDonnell, P., "The effect of dietary laminarin and fucoidan in the diet of the weanling piglet on performance, selected faecal microbial populations and volatile fatty acid concentrations," The Animal Consortium, Oct. 19, 2009, pp. 1-7.
McLearly, B., et al., "Measurement of B-Glucan in Mushrooms and Mycelial Products," McCleary & Draga: Journal of AOAC International, vol. 99, No. 2, Dec. 17, 2015, pp. 364-373.

(Continued)

*Primary Examiner* — Ruth A Davis
(74) *Attorney, Agent, or Firm* — Edwin S. Flores; Chalker Flores, LLP

(57) ABSTRACT

The present invention relates to compositions comprising at least about 8% β-glucans and/or at least about 8% α-fucans, which has a prebiotic effect and act as a replacement for in-feed antibiotics. The present invention also relates to extraction methods to obtain such extracts and various uses for the compositions comprising β-glucans and/or α-fucans.

20 Claims, 9 Drawing Sheets

(56) References Cited

OTHER PUBLICATIONS

O'Shea, C. J., et al., "Effect of the interaction of seaweed extracts containing laminarin and fucoidan with zinc oxide on the growth performance, digestibility and faecal characteristics of growing piglets," British Journal of Nutrition, Sep. 2, 2013, pp. 1-10.

O'Shea, C. J., et al., "The effect of algal polysaccharides laminarin and fucoidan on colonic pathology, cytokine gene expression and Enterobacteriaceae in a dextran sodium sulfate-challenged porcine model," Journal of Nutritional Science, Jan. 11, 2016, pp. 1-9.

Pielesz, A., et al., "Mild acid hydrolysis of fucoidan: characterization by electropheresis and FT-Raman Spectroscopy," Carbohydrate Research, vol. 346, May 30, 2011, pp. 1937-1944.

Walsh, A. M., et al., "Effect of supplementing varying inclusion levels of laminarin and fucoidan on growth performance, digestibility of diet components, selected faecal microbial populations and volatile fatty acid concentrations in weaned pigs," Animal Feed Science and Technology, vol. 183:3-4, Apr. 7, 2013, pp. 151-159.

Walsh A. M., et al., "Effect of dietary laminarin and fucoidan on selected microbiota, intestinal morphology and immune status of the newly weaned pig," British Journal of Nutrition, Feb. 16, 2013, pp. 1-9.

Hollants, et al., "What we can learn from sushi: a review on seaweed-bacterial associations," FEMS Microbiology Ecology 83, Jul. 30, 2012, pp. 1-16.

\* cited by examiner

FIG. 1

TABLE 1. COMPOSITION AND CHEMICAL ANALYSIS OF STARTER DIETS.

| DIET | STARTER | | | | | |
|---|---|---|---|---|---|---|
| TREATMENT | 1 | 2 | 3 | 4 | 5 | 6 |
| COMPOSITION (g/kg) | | | | | | |
| LACTOFEED* | 0 | 150 | 300 | 0 | 150 | 300 |
| GutCare ♦ | 0 | 0 | 0 | 5 | 5 | 5 |
| WHEAT | 572 | 427 | 287 | 567 | 422 | 282 |
| SOYA BEAN MEAL | 150 | 150 | 150 | 150 | 150 | 150 |
| WHEY PROTEIN | 125 | 125 | 125 | 125 | 125 | 125 |
| FULL FAT SOYA | 75 | 75 | 75 | 75 | 75 | 75 |
| SOYA OIL | 65 | 60.3 | 50 | 65 | 60.3 | 50 |
| MINERALS & VITAMINS | 5 | 5 | 5 | 5 | 5 | 5 |
| LYSINE | 4.5 | 4.5 | 4.05 | 4.5 | 4.5 | 4.05 |
| METHIONINE | 1.9 | 1.9 | 1.9 | 1.9 | 1.9 | 1.9 |
| THREOININE | 1.6 | 1.6 | 1.6 | 1.6 | 1.6 | 1.6 |
| ANALYSIS (g/kg) | | | | | | |
| DRY MATTER | 897.7 | 913.0 | 906.8 | 901.9 | 907.6 | 918.3 |
| CRUDE PROTEIN (N x 6.25) | 235.6 | 235.3 | 239.1 | 241.1 | 244.4 | 236.5 |
| GROSS ENERGY (MJ/kg) | 17.96 | 18.30 | 17.58 | 17.99 | 17.93 | 17.77 |
| ASH | 40.02 | 50.00 | 56.65 | 39.57 | 49.50 | 58.89 |
| NEUTRAL DETERGENT FIBRE | 131.32 | 103.01 | 96.02 | 127.72 | 108.69 | 83.44 |
| LYSINE■ | 16 | 16 | 16 | 16 | 16 | 16 |
| METHIONINE AND CYSTEINE■ | 9.6 | 9.6 | 9.6 | 9.6 | 9.6 | 9.6 |
| THREONINE■ | 12 | 12 | 12 | 12 | 12 | 12 |
| TRYPTOPHAN■ | 2.8 | 2.8 | 2.8 | 2.8 | 2.8 | 2.8 |
| CALCIUM■ | 9.0 | 9.0 | 9.0 | 9.0 | 9.0 | 9.0 |
| PHOSPHORUS■ | 7.0 | 7.0 | 7.0 | 7.0 | 7.0 | 7.0 |

*LACTOFEED 70 (VOLAC INTERNATIONAL LTD.) CONTAINS 860 g/kg OF WHEY PERMEATE AND 140 g/kg OF SOYA BEAN MEAL. LACTOFEED CONSISTS OF 955 g/kg DRY MATTER (DM); 700 g/kg OF LACTOSE; 125 g/kg OF CRUDE PROTEIN; 90 g/kg OF ASH; 50 g/kg OF OIL AND 10 g/kg OF CRUDE FIBRE.
♦BioAtlantis CO. KERRY.
■CALCULATED FROM PROXIMATE ANALYSIS (MINISTRY OF AGRICULTURE, FISHERIES AND FOOD, 1991).

TABLE 2. THE EFFECT OF DIETARY TREATMENT ON FAECAL DM, FAECAL pH, FAECAL SCORE, APPARENT DIGESTIBILITY COEFFICIENTS AND DIGESTIBLE ENERGY CONTENT OF STARTER DIETS (L.S.M +/-S.E.M)

| LACTOSE (g/kg) | 65 | 170 | 275 | 65 | 170 | 275 | SEM | SIGNIFICANCE | | |
|---|---|---|---|---|---|---|---|---|---|---|
| SEAWEED | - | - | - | + | + | + | | LACTOSE | GutCare | LACTOSE x GutCare |
| n | 6 | 6 | 6 | 6 | 6 | 6 | | | | |
| FAECES pH | | | | | | | | | | |
| DAYS 0-15 | 6.75 | 6.17 | 6.08 | 6.51 | 6.13 | 5.97 | | | | |
| DAYS 15-27 | 6.79 | 5.96 | 6.08 | 6.41 | 5.87 | 6.03 | | | | |
| DAYS 0-27 | 6.77 | 6.07 | 6.08 | 6.46 | 6.00 | 6.00 | 0.068 | *** | * | ns |
| FAECES SCORE | | | | | | | | | | |
| DAYS 0-8 | 3.00 | 2.77 | 2.71 | 2.79 | 2.75 | 2.68 | 0.151 | ns | ns | ns |
| DAYS 8-15 | 2.52 | 2.66 | 2.35 | 2.11 | 2.88 | 2.47 | 0.202 | ns | ns | ns |
| DAYS 15-21 | 1.90 | 1.94 | 2.05 | 2.03 | 2.00 | 1.74 | 0.020 | ** | * | *** |
| DAYS 21-27 | 2.02 | 1.90 | 1.80 | 1.99 | 2.40 | 2.12 | 0.122 | ns | * | ns |
| DAYS 0-27 | 2.36 | 2.32 | 2.23 | 2.23 | 2.51 | 2.25 | 0.100 | ns | ns | ns |
| DIGESTIBILITY (%) | | | | | | | | | | |
| DRY MATTER | 0.834 | 0.850 | 0.865 | 0.854 | 0.836 | 0.840 | 0.0055 | ns | ns | ** |
| ORGANIC MATTER | 0.848 | 0.863 | 0.877 | 0.867 | 0.850 | 0.855 | 0.0052 | ns | ns | ** |
| PROTEIN | 0.804 | 0.796 | 0.809 | 0.838 | 0.783 | 0.753 | 0.0102 | ** | ns | *** |
| ENERGY | 0.802 | 0.827 | 0.842 | 0.823 | 0.810 | 0.806 | 0.0064 | ns | ns | *** |
| NEUTRAL DETERGENT FIBRE | 0.478 | 0.457 | 0.503 | 0.543 | 0.419 | 0.383 | 0.0299 | * | ns | * |
| DIGESTIBLE ENERGY (MJ/kg) | 14.40 | 15.13 | 14.80 | 14.80 | 14.52 | 14.32 | | | | |

PROBABILITY OF SIGNIFICANCE; *, $P<0.05$; , $P<0.01$; *, $P<0.001$

FIG. 2

TABLE 3 COMPOSITION AND CHEMICAL ANALYSIS OF STARTER DIETS (AS FED)

| | TREATMENT | | | | | | | | | | | |
|---|---|---|---|---|---|---|---|---|---|---|---|---|
| | T1 | T2 | T3 | T4 | T5 | T6 | T7 | T8 | T9 | T10 | T11 | T12 |
| COMPOSITION g/kg | | | | | | | | | | | | |
| LACTOFEED[1] | 250 | 250 | 250 | 250 | 125 | 125 | 125 | 125 | 0 | 0 | 0 | 0 |
| WHEAT | 326 | 326 | 326 | 326 | 432 | 432 | 432 | 432 | 538 | 538 | 538 | 538 |
| SOYA BEAN MEAL | 150 | 150 | 150 | 150 | 167.5 | 167.5 | 167.5 | 167.5 | 185 | 185 | 185 | 185 |
| WHEY PROTEIN | 125 | 125 | 125 | 125 | 125 | 125 | 125 | 125 | 125 | 125 | 125 | 125 |
| FULL FAT SOYA BEAN | 60 | 60 | 60 | 60 | 60 | 60 | 60 | 60 | 60 | 60 | 60 | 60 |
| SOYA OIL | 70 | 70 | 70 | 70 | 72.5 | 72.5 | 72.5 | 72.5 | 75 | 75 | 75 | 75 |
| VITAMINS AND MINERALS[2] | 8 | 8 | 8 | 8 | 8 | 8 | 8 | 8 | 8 | 8 | 8 | 8 |
| METHIONINE † | 1.8 | 1.8 | 1.8 | 1.8 | 1.65 | 1.65 | 1.65 | 1.65 | 1.5 | 1.5 | 1.5 | 1.5 |
| LYSINE † | 5.5 | 5.5 | 5.5 | 5.5 | 4.95 | 4.95 | 4.95 | 4.95 | 4.4 | 4.4 | 4.4 | 4.4 |
| THREONINE † | 0.8 | 0.8 | 0.8 | 0.8 | 0.55 | 0.55 | 0.55 | 0.55 | 0.3 | 0.3 | 0.3 | 0.3 |
| CHROMIUM | 0.15 | 0.15 | 0.15 | 0.15 | 0.15 | 0.15 | 0.15 | 0.15 | 0.15 | 0.15 | 0.15 | 0.15 |
| GutCare | 0 | 3 | 6 | 12 | 0 | 3 | 6 | 12 | 0 | 3 | 6 | 12 |
| ANALYSIS g/kg | | | | | | | | | | | | |
| DRY MATTER | 873.6 | 898 | 895.9 | 899.1 | 907.2 | 893.7 | 897.9 | 892.5 | 886.3 | 985.4 | 890.3 | 887.9 |
| CRUDE PROTEIN (N x 6.25) | 194.7 | 198.2 | 201.8 | 196.8 | 199.5 | 204.5 | 202.7 | 201.5 | 205.7 | 209.9 | 212.9 | 213.9 |
| GROSS ENERGY (MJ/kg) | | | | | | | | | | | | |
| ASH | 48.44 | 48.46 | 48.98 | 49.33 | 43.46 | 43.78 | 43.57 | 44.82 | 36.23 | 37.89 | 38.42 | 38.9 |
| NEUTRAL-DETERGENT FIBRE | 64.52 | 66.4 | 67.3 | 66.95 | 73.75 | 70.13 | 75.09 | 72.57 | 78.76 | 79.43 | 89.64 | 81.54 |
| LACTOSE[3] | 243 | 243 | 243 | 243 | 153 | 153 | 153 | 153 | 63 | 63 | 63 | 63 |
| LYSINE | | | | | | | | | | | | |

[1] THE LACTOFEED WAS MANUFACTURED BY VOLAC INTERNATIONAL LTD, ORWELL, UNITED KINGDOM. THE CHEMICAL ANALYSIS IS AS FOLLOWS: (g/kg) DRY MATTER 955, CRUDE PROTEIN 125, OIL 50, ASH 90, FIBRE 10, GROSS ENERGY CONTENT 15.5 MJ kg AND A pH OF 6.5-7.

[2] PROVIDED (mg/kg COMPLETED DIET): Cu 175, Fe 140, Mn 47, Zn 120, I 6, Se 0.3, RETINOL 1.8, CHOLECALCIFEROL 0.025, ALPHA-TOCOPHEROL 67, PHYTYLMENAQUINONE 4, CYANOCOBALAMIN 0.01, RIBOFLAVIN 2, NICOTINIC ACID 12, PANTOTHENIC ACID 10, CHOLINE CHLORIDE 250, THIAMINE 2, PYRIDOXINE 0.015. CHROMIUM III OXIDE INCLUDED AT 200 mg/kg COMPLETE DIET.

[3] CALCULATED CONCENTRATION OF LACTOSE.

† CALCULATED FROM PROXIMATE ANALYSIS. (MINISTRY OF AGRICULTURE, 1991)

FIG. 3

TABLE 4 THE EFFECT OF LACTOSE LEVEL AND GutCare CONCENTRATION ON PIG PERFORMANCE AFTER WEANING (DAY 0) (LEAST SQUARE MEANS AND s.e.)

| | | | | | | | | | | | | | | SIGNIFICANCE | |
|---|---|---|---|---|---|---|---|---|---|---|---|---|---|---|---|
| GutCare (g/kg) | 0 | 3 | 6 | 12 | 0 | 3 | 6 | 12 | 0 | 3 | 6 | 12 | s.e. | GutCare | LACTOSE x β-Glucan |
| LACTOSE LEVEL (g/kg) | 243 | 243 | 243 | 243 | 153 | 153 | 153 | 153 | 63 | 63 | 63 | 63 | | | |
| NO. OF PENS | 8 | 8 | 8 | 8 | 8 | 8 | 8 | 8 | 8 | 8 | 8 | 8 | | | |
| FOOD INTAKE (g/day) | | | | | | | | | | | | | | | |
| DAYS 0-7 | 263 | 301 | 268 | 226 | 255 | 236 | 242 | 265 | 213 | 200 | 257 | 207 | 19 | ns | * |
| DAYS 7-14 | 476 | 541 | 589 | 494 | 488 | 547 | 503 | 581 | 438 | 420 | 508 | 454 | 24 | * | ns |
| DAYS 14-21 | 743 | 838 | 901 | 827 | 788 | 818 | 790 | 871 | 733 | 723 | 814 | 738 | 48 | * | ns |
| DAYS 0-21 | 494 | 560 | 586 | 516 | 510 | 533 | 512 | 573 | 461 | 447 | 526 | 467 | 25 | * | ns |
| DAILY GAIN (g/day) | | | | | | | | | | | | | | | |
| DAYS 0-7 | 175 | 246 | 214 | 182 | 163 | 141 | 187 | 188 | 91 | 141 | 181 | 159 | 32 | * | * |
| DAYS 7-14 | 326 | 387 | 392 | 369 | 279 | 366 | 378 | 370 | 255 | 240 | 299 | 298 | 26 | * | ns |
| DAYS 14-21 | 467 | 515 | 510 | 489 | 506 | 503 | 519 | 523 | 401 | 440 | 460 | 451 | 28 | * | ns |
| DAYS 0-21 | 323 | 383 | 372 | 347 | 316 | 337 | 361 | 360 | 249 | 274 | 313 | 303 | 23 | ** | * |
| FOOD CONVERSION RATIO | | | | | | | | | | | | | | | |
| DAYS 0-7 | 1.58 | 1.2 | 1.52 | 1.27 | 1.94 | 2.18 | 1.29 | 1.85 | 2.52 | 2.21 | 1.56 | 1.26 | 0.333 | * | * |
| DAYS 7-14 | 1.51 | 1.46 | 1.56 | 1.34 | 1.8 | 1.55 | 1.37 | 1.69 | 1.81 | 1.93 | 1.69 | 1.6 | 0.138 | ns | ns |
| DAYS 14-21 | 1.6 | 1.63 | 1.75 | 1.7 | 1.56 | 1.65 | 1.51 | 1.73 | 1.85 | 1.69 | 1.78 | 1.96 | 0.121 | ns | ns |
| DAYS 0-21 | 1.57 | 1.46 | 1.61 | 1.45 | 1.76 | 1.79 | 1.4 | 1.76 | 2.05 | 1.95 | 1.69 | 1.54 | 0.138 | * | † |

† = (P<0.1), * = (P<0.05),  = (P<0.01), * = (P<0.001), ns = NON SIGNIFICANT (P>0.05).

FIG. 4

TABLE 5 THE EFFECT OF GutCare ON SELECTED MICROBIAL POPULATIONS IN THE CAECUM AND COLON OF THE PIGLET (LSM +/- s.e.m)

| GutCare | NONE | GutCare | s.e. |
|---|---|---|---|
| CAECUM | | | |
| BIFIDOBACTERIA | 7.541 | 6.450 | 0.315 |
| E.coli | 4.628 | 1.211 | 0.867 |
| LACTOBACILLI | 7.293 | 6.305 | 0.308 |
| COLON | | | |
| BIFIDOBACTERIA | 7.670 | 6.900 | 0.346 |
| E.coli | 5.235 | 1.835 | 0.814 |
| LACTOBACILLI | 7.837 | 6.786 | 0.213 |

FIG. 5

TABLE 6. COMPOSITION AND ANALYSIS OF EXPERIMENTAL DIETS.

| TREATMENT | 1 | 2 | 3 | 4 | 5 |
|---|---|---|---|---|---|
| COMPOSITION (g/kg) | | | | | |
| GutCare | 0 | 0.7 | 1.4 | 2.8 | 5.6 |
| WHEAT | 704.3 | 704.3 | 704.3 | 704.3 | 704.3 |
| SOYA BEAN MEAL | 264.7 | 264.7 | 264.7 | 264.7 | 264.7 |
| SOYA OIL | 5.7 | 5.7 | 5.7 | 5.7 | 5.7 |
| LIMESTONE FLOUR | 15.0 | 15.0 | 15.0 | 15.0 | 15.0 |
| DICALCIUM PHOSPHATE | 7.5 | 7.5 | 7.5 | 7.5 | 7.5 |
| MINERALS & VITAMINS† | 25.0 | 25.0 | 25.0 | 25.0 | 25.0 |
| ANALYSIS (g/kg) | | | | | |
| TOTAL β-glucan | 0 | 0.089 | 0.178 | 0.356 | 0.712 |
| DRY MATTER | 869.1 | 871.8 | 886.5 | 884.4 | 878.2 |
| CRUDE PROTEIN | 215.7 | 203.2 | 199.5 | 200.8 | 195.1 |
| NEUTRAL DETERGENT FIBRE | 119.7 | 97.8 | 91.8 | 96.4 | 98.0 |
| ACID DETERGENT FIBRE | 39.0 | 35.2 | 30.7 | 32.7 | 35.7 |
| HEMI CELLULOSE | 80.7 | 62.6 | 61.1 | 63.7 | 62.3 |
| CRUDE ASH | 45.7 | 48.4 | 47.7 | 51.2 | 52.6 |
| GROSS ENERGY (MJ/kg) | | | | | |
| LYSINE ‡ | 10.0 | 10.0 | 10.0 | 10.0 | 10.0 |
| METHIONINE AND CYSTEINE ‡ | 6.0 | 6.0 | 6.0 | 6.0 | 6.0 |
| THREONINE ‡ | 6.8 | 6.8 | 6.8 | 6.8 | 6.8 |
| TRYPTOPHAN ‡ | 1.8 | 1.8 | 1.8 | 1.8 | 1.8 |

‡ CALCULATED FROM MINISTRY OF AGRICULTURE, FISHERIES AND FOOD (1991).

† PROVIDED PER kg OF COMPLETE DIET: 3mg RETINOL, 0.05 mg CHOLECALCIFEROL, 40 mg ALPHA-TOCOPHEROL, 90 mg COPPER AS COPPER II SULPHATE, 100 mg IRON AS IRON II SULPHATE, 100 mg ZINC AS ZINC OXIDE, 0.3 mg SELENIUM AS SODIUM SELENITE, 25 mg MANGANESE AS MANGANOUS OXIDE AND 0.2 mg IODINE AS CALCIUM IODATE ON A CALCIUM SULPHATE/CALCIUM CARBONATE CARRIER

FIG. 6

TABLE 7: EFFECT OF GutCare CONCENTRATION ON MICROBIAL ECOLOGY IN THE COLON, CFU (LSM ± s.e.m.)

| TREATMENT | 1 | 2 | 3 | 4 | 5 | s.e.m | SIGNIFICANCE | |
|---|---|---|---|---|---|---|---|---|
| GutCare (g/kg) | 0 | 0.7 | 1.4 | 2.8 | 5.6 | | LINEAR[b] | QUADRATIC[c] |
| COLON BACTERIAL POPULATIONS | | | | | | | | |
| *ENTEROBACTERIA* | 6.95 | 6.72 | 6.34 | 6.49 | 6.85 | 0.245 | ns | * |
| *BIFIDOBACTERIA* | 8.37 | 8.62 | 8.69 | 8.80 | 8.16 | 0.110 | ns | *** |

\* = ($P<0.05$),  = ($P<0.01$), * = ($P<0.001$), ns = NON SIGNIFICANT ($P>0.05$)

[b] LINEAR: LINEAR RESPONSE TO GutCare

[c] QUADRATIC RESPONSE TO GutCare

FIG. 7

TABLE 8: EFFECT OF GutCare CONCENTRATION ON TOTAL TRACT DIGESTIBILITY COEFFICIENTS (LSM ± s.e.m.)

| TREATMENT | 1 | 2 | 3 | 4 | 5 | s.e.m | SIGNIFICANCE | |
|---|---|---|---|---|---|---|---|---|
| | | | | | | | LINEAR[b] | QUADRATIC[c] |
| GutCare (g/kg) | 0 | 0.7 | 1.4 | 2.8 | 5.6 | | | |
| TOTAL TRACT DIGESTIBILITY | | | | | | | | |
| ASH | 0.57 | 0.62 | 0.56 | 0.62 | 0.62 | 0.010 | ** | ns |

\* = ($P<0.05$),  = ($P<0.01$), * = ($P<0.001$), ns = NON SIGNIFICANT ($P>0.05$)

[b] LINEAR: LINEAR RESPONSE TO GutCare

[c] QUADRATIC RESPONSE TO GutCare

FIG. 8

TABLE 9 THE EFFECTS OF DIETARY TREATMENT ON FAECAL DRY MATTER (DM), FAECAL pH AND FAECAL SCORE IN PIGLETS (LEAST SQUARE MEANS AND s.e.)

| GutCare | 0 | 3 | 6 | 12 | 0 | 3 | 6 | 12 | 0 | 3 | 6 | 12 | | SIGNIFICANCE | |
|---|---|---|---|---|---|---|---|---|---|---|---|---|---|---|---|
| LACTOSE LEVEL (g/kg) | 243 | 243 | 243 | 243 | 153 | 153 | 153 | 153 | 63 | 63 | 63 | 63 | s.e. | LACTOSE | GutCare |
| | (T1) | (T2) | (T3) | (T4) | (T5) | (T6) | (T7) | (T8) | (T9) | (T10) | (T11) | (T12) | | | |
| NO. OF PENS | 8 | 8 | 8 | 8 | 8 | 8 | 8 | 8 | 8 | 8 | 8 | 8 | | | |
| FAECAL DM (g/kg) | 26.01 | 26.59 | 27.81 | 27.47 | 21.82 | 27.49 | 27.31 | 25.87 | 24.36 | 26.35 | 24.77 | 25.69 | 1.7890 | ns | ns |
| FAECAL pH | 6.23 | 6.07 | 6.05 | 5.9 | 6.4 | 6.12 | 6.24 | 6.06 | 6.63 | 6.42 | 6.52 | 6.59 | 0.0750 | *** | ns |
| FAECAL SCORE ‡ | | | | | | | | | | | | | | | |
| DAYS 0-7 | 2.73 | 2.25 | 2.63 | 2.55 | 2.85 | 2.33 | 2.15 | 2.6 | 2.73 | 2.45 | 2.73 | 2.25 | 0.2080 | ns | † |
| DAYS 7-14 | 2.73 | 2.48 | 2.8 | 2.4 | 3.03 | 2.38 | 2.25 | 2.78 | 2.63 | 2.68 | 2.68 | 2.53 | 0.2110 | ns | ns |
| DAYS 14-21 | 2.54 | 2.24 | 2.67 | 2.34 | 2.72 | 2.25 | 2.16 | 2.43 | 2.64 | 2.69 | 2.85 | 2.37 | 0.1800 | * | ns |
| DAYS 0-21 | 2.66 | 2.32 | 2.7 | 2.43 | 2.86 | 2.32 | 2.19 | 2.6 | 2.66 | 2.61 | 2.75 | 2.38 | 0.1760 | ns | ns |

† = ($P<0.1$), * = ($P<0.05$),  = ($P<0.01$), * = ($P<0.001$), ns = NON SIGNIFICANT ($P>0.05$).
‡ 1 = HARD FAECES AND 5 = WATERY, MUCOUS-LIKE FAECES.

FIG. 9

COMPOSITION TO IMPROVE GUT HEALTH AND ANIMAL PERFORMANCE AND METHODS OF MAKING THE SAME

CROSS-REFERENCE TO RELATED APPLICATIONS

This application is a continuation application of Ser. No. 15/905,361 filed on Feb. 26, 2018, which claims priority to and is a continuation of U.S. patent application Ser. No. 12/094,383, filed Nov. 14, 2008, which is a National Stage Entry of PCT/IE2006/000131, filed Nov. 21, 2006, which claims priority to IE S2005/0772 filed on Nov. 21, 2005, the entire contents of which are incorporated herein by reference.

FIELD OF THE INVENTION

This invention relates to nutraceutical formulations and the extraction processes used to obtain them. In another aspect, this invention relates to the prebiotic effect of β-glucans and/or α-fucans and the potential thereof for acting as replacements for in-feed antibiotics. This invention may also result in an increase in the levels of helpful microbes and a corresponding reduction in the level of harmful microbes in the gut. Other aspects of this invention relate to the improvement in nutrient digestibility and increased absorption of minerals and micronutrients in the host, and an improvement in animal performance in terms of increased weight gain, improved feed conversion ratios and greater daily intakes.

In another aspect, this invention relates to human prebiotics and the development of a novel composition to be given to humans to increase levels of beneficial bacteria in the human gut.

The invention also provides a synbiotic (consisting of a prebiotic along with a probiotic) composition which when given to humans helps to restore helpful bacteria and boost their growth in the human gut.

BACKGROUND TO THE INVENTION

The beneficial growth promoting effects of antimicrobials in animal feed to minimise disease have been known since the 1940s. However, the Swann report (1969) requested a more strict government control on the use of antibiotics in feed. Since the Swann report, there has been increasing concern about the transmission of resistant bacteria and this has resulted in the EU ban on antibiotic growth promoters taking effect from the 1 Jan. 2006. This ban on antibiotic growth promoters will unquestionably affect disease control on farms as well as animal performance and necessitates effective alternatives. The removal of antibiotics from animal feed will also lead to an increase in the proportions of harmful microbes like E. coli and Salmonella in the gut microflora of farm animals.

Even in the current scenario, the number of cases of food poisoning in developed countries like Ireland has increased over the last decade with Campylobacter spp. infection being the most common and Salmonella spp. infection the second most common cause of illness. New salmonella control measures are being introduced to Ireland and these control measures will cause serious difficulties for some animal, cattle, poultry and pig producers.

Current intensive farming techniques have also lead to an increase in stress related disorders in farm animals, including poor gut health and a high incidence of diseases like PMWS. Weaning constitutes one of the most stressful situations in the life of the pig (Melin et al., 2004). The young pig is subjected to a myriad of stressors (Pluske et al., 1997) which leads to impaired immune function and an increased susceptibility towards infections (Hiss et al., 2003). The use of infeed antibiotics has reduced these problems due to a reduction in the microbial population within the gastrointestinal tract, as well as a change from pathogenic towards beneficial bacteria. This results in better nutrient absorption, less substrate for the proliferation of pathogenic organisms and an improvement in the health status and integrity of the gastrointestinal tract (Close, 2000). However, as a result of various public health scares associated with animal product consumption there is increasing consumer pressure to reduce the use of antibiotics (Williams et al, 2001). There therefore exists an urgent need to find alternatives to in-feed antibiotics that can give the above mentioned benefits, without adversely affecting human health.

Given the cost pressures in intensive farming, animal performance, particularly at early stages of growth, are of crucial importance to the farmer. In this regard, the key parameters to be considered include the average daily gain (weight gain per piglet per day), the feed conversion ratio (a measure of the performance efficiency of the piglet), the average daily intake (grams of food intake/day) and a reduction in scouring (a measure of the consistency of the feces, and an indicator of diarrhea in the young pig). Any composition that seeks to improve performance should effect an increase in the ADG, an improvement in the FCR (as indicated by a reduction in its value) and a reduction in scouring (indicated by more solid feces).

Similarly, unhealthy eating habits in humans have had a huge impact on gut health. In a recent survey of European manufacturers (Leatherhead R. A Survey), 21% said that gut health would have the greatest influence on the functional food market. Thus, there exists a need for a composition that can improve the gut health of humans and act as a prebiotic for beneficial bacteria.

Replacement of antimicrobials: There are a number of alternative strategies that are available as replacement products for in-feed antibiotics and salmonella control, including diet acidification, inclusion of various probiotics into the diet, fructo-oligosaccharides, enzymes and herbs.

Dietary acidification using organic acids is the most common strategy currently being used. This is believed to have an important function improving digestion and assisting the microbial balance in the intestinal tract. The beneficial effects of these vary according to type, the strongest acid being formic acid. A low pH is required to activate critical digestive enzymes in the stomach of the pig. Also one of the greatest barriers to the invasion of the intestinal tract by pathogenic bacteria is acidic pH. However, acids have limited use unless they are protected in the stomach as otherwise they are likely to be neutralized by the enzymes in the upper digestive tract. Furthermore, as the pig grows, its ability to naturally produce sufficient acid for digestion increases thus reducing the benefit of an acidifier. Thus, acids are useful additives only in the diet of small pigs and pigs fed low quality diets.

Also, where high density diets high in ingredients derived from milk have been used the response to acid addition has been much less. This is because the lactose in milk is converted to lactic acid creating desirable changes in the gastric environment, thus reducing the need for additional acidification. However, lactose is an expensive dietary component, and there exists a need to discover components that can limit the amount of lactose required in the diet, while enhancing its beneficial effects. Furthermore, high levels of lactose make diets difficult to prepare, as lactose is hygroscopic and difficult to deal with, especially at high levels.

Another common strategy being used is the introduction of probiotics (or direct-fed microbials) in animal diets. However, the development of probiotics is limited by certain restraining factors including stringent European legislation on the use of probiotics and a wide range of alternate ingredients. Furthermore, animal feed products are often treated at high temperatures and probiotics (being microbial in nature) cannot survive such temperatures.

Fructose oligosaccharides (FOS), prebiotics currently being sold in the pig market, have several advantages. However, some researchers (Jaskari et al, 1998) have questioned the selectivity of FOS as a substrate for beneficial carbohydrate bacteria. In in-vitro trials, they have been found to increase the growth of all bacteria (including bactericides found naturally in the gut as well as *E. coli*), thus raising doubts over their selectivity. Thus FOS may in themselves, not be an ideal solution.

None of these strategies match antimicrobials in terms of performance and all give very variable results. There therefore exists a need to provide a food supplement that can act as an alternative to antibiotics and improve animal performance.

Impact of unhealthy diets in humans: There has been an increased tendency in recent years to increase the levels of protein in human diets. This tendency is exacerbated by the existence of high protein diets, like the Atkins diet, that increase the levels of protein in the diet while reducing the levels of carbohydrates. Such diets have a profound influence on the gut microflora and increase the levels of protein fermenting bacteria like *E. coli* and *Salmonella*, while reducing the levels of beneficial carbohydrate fermenting bacteria like the *lactobacilli* and the *bifidobacteria* (Lynch et al unpublished) Therefore, there exists a need for compositions that can restore the balance of microflora in the gut and can boost the incidence of beneficial bacteria. The key strategy being followed currently is the use of probiotics, which are particular strains of microbes fed directly to the individual. However, the human gut flora consists of over 400 species of bacteria and probiotics can only aim to re-introduce a few of these species. Current prebiotics, like insulin are non-specific and may in fact boost the levels of harmful bacteria like *E. coli* (Jaskari et al, 1998, Pierce at al, 2005), while increasing the levels of beneficial bacteria like *bifidobacteria*. Therefore, there exists a need for a prebiotic composition that can selectively boost the levels of beneficial carbodydrate fermenting bacteria like the *bifidobacteria* while reducing the levels of *E. coli* and *Salmonella*.

DESCRIPTION OF RELATED ART

Definitions

A prebiotic is defined as a non-digestible food ingredient that beneficially affects the host by selectively stimulating the growth and/or activity of one or more of bacteria. The non-digestibility of prebiotics ensures that they can reach the colon and act as an energy source for bacteria, unlike normal sugars, which get digested directly by the host (Gibson et al, 1995).

β-glucans are homopolysaccharides of linear or branched glucose residues. β-(1,3) glucans are a naturally occurring class of polysaccharides found in many species of yeast (including Baker's Yeast or *S. cerevisiae*), mushrooms, plants (including cereals) and some bacterial, lichen and algal species (particularly brown algae or the *Ascophyllum* and *Laminaria* families). However, the structure and physiological properties of the glucans found in these sources is quite different with the beta glucans isolated from cereal sources (like wheat, barley and oats) being linear homopolysaccharides (of glucose) with approximately 70% (1,4)-linkages and 30% (1,3)-linkages (Cui et al, 2000 and MacGregor and Rattan, 1993), while the glucans isolated from yeast consists predominantly of β-(1,3) glucan chains with β-(1,6) branching as well as a small incidence of (3-(1,6) linked chains. (Magnelli et al, 2002).

Algal β-glucans, called laminarin, consist of β-(1,3)-D glucan with occasional (1,6) linked branches. Laminarin from *Laminaria digitata* occurs as two homologous series of molecules, a minor G series containing 22-28 glucosyl residues and a more abundant M series consisting of 20-30 glucosyl residues linked to a mannitol residue. Laminarin from many species of *Laminaria* (including *Laminaria hyperborea*) is insoluble and consists of predominantly β-(1,3) chains while the laminarin from *Laminaria digitata* is soluble and consists of small but significant levels of (3-(1,6) linked branches. (Read et al, 1996).

The β-glucans found in yeast are long linear chains of up to 1300-1500 residues of glucan molecules linked by a β-(1,3) bond with a minor incidence of β-(1,6) chains (which are much smaller and have only about 140 residues). Algal β-glucans on the other hand (also called laminarin) have much smaller chain lengths (average residue size of only 24 residues) with occasional β-(1,6) branches depending on the species. *Laminaria digitata* has the 1,6 branching which make the glucans derived from them water soluble. Other *laminaria* species like *hyperborea* do not have this branching which makes the linear chains aggregate and makes the glucans extracted from it, predominantly insoluble.

Natural polysaccharides built up essentially of sulfated alpha-L-fucose residues are known as fucoidans (or α-fucans). These are present in brown algae, some echinoderms and are the predominant polysaccharide in brown seaweed, like *Ascophyllum nodosum* and the *Laminaria* spp. Fucoidans (α-fucans) have been extensively studied due to their diverse biological activities, since they are potent anticoagulant, antitumor, and antiviral agents.

DESCRIPTION OF PRIOR ART

U.S. Pat. No. 4,891,220 discloses methods and compositions to lower serum lipid levels using yeast glucans which are cholesterol-lowering agent. Similarly, U.S. Pat. No. 6,143,731 discusses the ability of yeast glucans to act as a source of fiber, reduce the level of serum cholesterol, increase HDL cholesterol levels and act as bulking agents in humans and animals. Similarly, Hogberg et al (2005) discuss the alteration of the molar proportions of various short chain fatty acids and lactic acid in pigs fed cereal 3-glucans and other non-starch polysaccharides. However, there is no disclosure of the influence of these Non Starch Polysaccharides (NSPs) on mineral absorption or on any of the performance and prebiotic parameters mentioned above. Also, a mixture of various non-starch polysaccharides was tested in this work, unlike the research disclosed in this document, where two specific NSPs are tested.

Many researchers have also indicated the prebiotic effect of cereal β-glucans (i.e. 1, 3-1,4 mixed linked β-glucans) as selective substrates for beneficial bacteria, particularly of the *Lactobacillus* spp. Jaskari et al (1998) indicate how diets based on different cereals supply diverse substrates for microbial fermentation in-vitro. Charalampopoulos et al (2002) discuss the application of cereals and cereal components (including cereal beta glucans) in functional foods. Martensson et al (2005) discuss the ability of fermented oat based product containing native oat β-glucans and glucans derived from *Pediococcus damnosus* to reduce cholesterol levels in humans and also stimulate the *bifidobacteria* flora. *Pediococcus* sp. produces a glucan exo-polysaccharide which contains a β-(1,3)(1,2) tri-saccharide repeating unit (Llauberes et al, 1990). However, none of these researchers have indicated a prebiotic effect for β-(1,3) (1,6) glucans or the ability of these glucans to act as a selective substrate for beneficial bacteria, especially of the *bifidobacteria* spp.

Various researchers have also looked at the effect of β-glucans fed to animals on animal performance. US 20050020490 discusses the ability of yeast glucans to improve the growth rate during an immune system challenge. US 20030219468 discusses the beneficial effects of 3-glucans, combined with sorbic acid, on the hygiene state of feed as well as the growth performance of animals fed the combination. U.S. Pat. No. 6,939,864 discusses the synergistic effects of yeast β-glucans and ascorbic acid on animal growth and well-being. U.S. Pat. No. 6,214,337 relates to the beneficial effects of yeast glucans on pig performance, when fed in combination with an antibiotic. None of the above researchers have looked at the effects of the algal polysaccharides, laminarin and fucoidan on animal performance or the effect of a combination of these glucans on animal performance (as the combination may have effects quite distinct from the components administered alone).

Most researchers indicate a negative correlation between high levels of NSPs in the diet and animal performance. Hogberg et al (2005) report a higher growth rate for pigs fed lower quantities of NSP. Bergh et al (1999) also report an anti-nutritional effect of barley β-glucan in poultry nutrition. Thus, the beneficial effects of cereal β-glucans on animal performance are unclear. The effects of beta glucans and NSPs may be dependent on the solubility and bioavailability of the non starch polysaccharides. The inventors have found that algal polysaccharides, when given as a combination, surprisingly, boost animal performance instead of depressing it, which is an improvement over the prior art.

Other researchers (Petersson and Lindberg, 1997) have also looked at the digestibility of cereals, particularly barley, and of the β-glucans they contain. Hogberg et al (2005) report a lower coefficient of caecal and total tract digestibility of organic matter in diets containing high amounts of non starch polysaccharide than in diets containing lower amounts of the same. Bergh et al (1999) also reported an increased ileal digestibility of nutrients in barley based diets when the 3-glucans were hydrolyzed with a glucanase enzyme. Thus the research seems to indicate a negative correlation between the amount of non starch polysaccharide (including β-glucans) in the diets and nutrient digestibility. However, the direct impact of (1,3) (1,6) β-glucans and other algal polysaccharides like fucoidan on digestibility has never been elucidated. Again, the composition in the current patent improves digestibility, an improvement over the prior art in this regard.

Hayen et al in U.S. Pat. No. 6,214,337 refer to the addition of yeast glucans to animal feed to improve animal growth. The glucans used are β(1,3)- and β(1,6)-glucans derived from yeast such as, for example, *Saccharomyces cerevisiae*. They measure the effects of these glucans, when used synergistically with the antibiotics, and do not propose the glucans as replacements for antibiotics.

A major point of difference between the prior art and the current work is that many of the prior art trials were conducted in the presence of in-feed antibiotics and plasma/bloodmeals in the diets. The results obtained with these diets are likely to be substantially different than results obtained without them. In fact, the present invention is motivated by the need to find replacements for antibiotics and is not concerned with physiological effects observed in the presence of such compounds.

Other patents and patent applications generally related to the field are U.S. Pat. Nos. 5,591,428, 6,841,181, 5,622,939, US 20040253253, US 20010016220, US 20030124170, US 20040138172, US 20040058889, US 20050058671, US 20050118326, US 20050020490 and US 20020146484.

Seaweed Extracts

There is considerable interest in western society in the possible health benefits of eating seaweed and seaweed extracts (see for example http://www.whfoods.com). A number of compounds from seaweed, such as carrageenan, chitin and agar, have been reported to improve gut health in humans and act synergistically with a prebiotic. E.g. US 20040086491 refers to a human prebiotic and probiotic mixture that also consists of the oligosaccharides carrageenan, chitin and agar as well as the non-starch polysaccharide, insulin, a well known prebiotic compound. Alginate, another polysaccharide from algae has been reported to have various benefits, including positive effects on gastrointestinal and cardiovascular health, and may act as a dietary fiber (Brownlee et al., 2005). However, the levels of alginate tested are much higher than those contained in the current composition. Furthermore, studies on a potential prebiotic effect have been inconclusive.

However, the prebiotic effects of the polysaccharides derived from brown algae, particularly laminarin and fucoidan, in in-vivo systems, have never been explored. C. Michel et al, 1996 refer to the degradation of algal fiber by human fecal bacteria. However, this in-vitro response cannot be extrapolated to indicate a prebiotic effect in mammals for various reasons. Firstly, the experiment conducted by the group did not mimic the enzymes and conditions of the digestive system, which could alter the fibers in a way that makes them more or less susceptible to bacterial fermentation. Secondly, fecal bacteria do not represent the full component of human digestive bacteria. Furthermore, the fibers may be degraded in the upper digestive tract and may never reach the target microbial population in the lower digestive tract. Also, the paper mentioned above does not deal with swine intestinal bacteria, unlike the present research.

A suitable source of the active ingredients of this application is seaweed, particularly brown algae. US 2003119780, US 20050065114 and US 20050095250 discuss methods of producing laminarin with an anti-cancer application, either by extracting the laminarin from seaweed or by synthesizing small molecule laminarin analogues. The method used to extract laminarin consists usually of an acid hydrolysis step followed by centrifugation followed by ultrafiltration to get the purified laminarin of the desired molecular size. Laminarin from certain seaweeds such as *Laminaria digitata* has the advantage that it is water soluble, reducing the need for an additional solubilization step in the process.

For the purposes of this invention, a specific conformation of laminarin/glucan is not required as the prebiotic or anti-microbial action is not determined by its three-dimensional conformation but the nature of the bond and the chain length. The laminarin need not be separated from additional algal sugars like fucoidan or sugar alcohols like mannitol, as they have beneficial biological actions of their own and act synergistically with laminarin to improve gut health.

The nutritional uniqueness of seaweed also involves a category of nutrients called sulfated polysaccharides. These carbohydrate-related nutrients, also called fucans, have been studied for their anti-inflammatory properties, and fucan extracts from brown sea-vegetables have been found to inhibit human complement activation in-vitro (Blonden et al, 1995).

Laminarins, both naturally extracted and synthetically derived, have also been investigated for their immunological properties and US 20050208079 mentions these effects as well as methods of preparing such biologically active extracts. US 2005095250 discusses the anti-cancer effect of laminarin, when applied in combination with a monoclonal antibody while US 20030119780 discusses these effects for laminarin alone. US 20050065114 discusses the antitumor effects of short chain laminarin analogues and methods of preparing the same. US 20040127457 discusses the anti-inflammatory action of laminarin. All these applications depend on the immuno-stimulating properties of laminarin for their action.

Turner et al, 2002 found a slight improvement in growth performance and no immune response in pigs fed *Ascophyllum nodosum* extract. However, they do not mention the nature of the extract (acid or alkaline) or the composition of the extract. Thus it is difficult to speculate which components in the extract were responsible for the results. As is indicated elsewhere in this document, the extraction method has a large bearing on the composition of the resulting extract.

None of the prior art compositions teach the use of β-glucans or α-fucans, singly or in combination for improved mineral and micronutrient absorption. Furthermore, none of the above refer to the use of Beta (1,3) (1,6) glucans or α-fucans, singly or in combination as prebiotics in mammals, as a means to reduce the threat of *E. coli* and *Salmonella* infection (particularly in weaned pigs) and as a means to improve ileal and apparent nutrient digestibility. Nor do they refer to the benefits of β-glucans and α-fucans, particularly those derived from seaweed, as means to improve pig performance and act as replacements for in-feed antibiotics in pigs.

There are various existing reports in literature of processes for obtaining extracts from seaweed, e.g. GB 727013 discloses a process for extracting laminarin, mannitol and alginic acid from various kinds of seaweed. Mabeau et al, 1987 refer to a process for extracting polysaccharides from seaweed, especially fucans like fucoidan. S. Colliec et al, 1994 also give a process for extracting crude fucoidan from seaweed by acid treatment. Zvyagintseva et al, 1999 report a procedure for obtaining water-soluble polysaccharides from seaweed using hydrophobic chromatography. However, most of these processes are either too expensive to be carried out on a commercial scale (e.g., the processes involving chromatography) or have yields that are uneconomical on a large scale.

Thus, there also exists a need for a prebiotic composition that can be economically extracted and is biologically active as a prebiotic in humans or animals. There is also a need for a prebiotic composition with high levels of β-(1,3)(1,6)-glucans and/or α-fucans, and a process for obtaining it.

OBJECT OF THE INVENTION

It is an object of the present invention to provide a novel composition that can act as a prebiotic feed supplement and improve gut health in humans and animals. A further object is the extraction of novel compositions that can be used as feed supplements from the group consisting of seaweed, barley, yeast, oats, mushrooms and other fungi/microbes.

It is a further object of the invention that the feed supplement provides a means for regulation of the gut microflora to aid in the growth of beneficial microbes; and/or a means for acidification of the gut leading to an improvement in gut health and/or a reduction in the growth of pathogenic bacteria (particularly in small pigs). Other aspects of this invention relate to an improvement in the absorption of minerals in the hind gut as well as an improvement in animal performance. Aspects of the invention are particularly useful in improvements in pig, cattle and poultry husbandry.

Further objects of the invention relate to the beneficial effect of β-glucans and/or α-fucans derived from natural materials and their potential as replacements for in-feed antibiotics.

It is also an object of the invention to provide human prebiotics and novel compositions for humans to increase levels of helpful bacteria in the human gut. The invention also provides a symbiotic (consisting of a prebiotic along with a probiotic) given to humans to restore helpful bacteria and boost their growth in the gut.

It is also an object of the invention to provide a novel extraction process to obtain a prebiotic feed supplement from seaweed in an economical manner that can be performed easily at a large scale. It is also an object to provide a method of obtaining such a composition consisting of a novel nanofiltration step.

SUMMARY OF THE INVENTION

The inventors have found that a particular composition, consisting of a high proportion of β-glucans and α-fucans is able to act as an anti-microbial, particularly in young mammals (reducing the threat of infections like *E. coli* and *Salmonella*) and improve animal performance. This composition also acts as a prebiotic in humans and other large mammals and selectively boosts the growth of beneficial microbes. It also improves mineral absorption in the hind gut and increases nutrient digestibility. This is a large improvement over the art as, currently, there is no single composition that can concomitantly achieve all these objectives.

Composition

In one aspect, the present invention relates to a composition comprising at least about 8% by weight β-glucans or at least about 8% α-fucans or a mixture thereof. Preferably, the β-glucans are present in an amount of between about 8% and about 30% by weight. Ideally, for some applications, the β-glucans comprise β-(1,3)(1,6)-glucans. Favourably, these are derived from seaweed and/or yeast. In preferred embodiments of the invention, the β-glucan present is Laminarin, although alternative β-glucans such as scleroglucan and PSAT are encompassed by the invention. Laminarin is the storage polysaccharide of *Laminaria* and other brown algae; and is primarily made up of β-(1-3)-glucan with some β-(1-6) linkages. Other sources of β-glucans include yeast extracts, mushrooms, barley and oats.

Preferably, the α-fucans are present in an amount of between about 8% and about 30% by weight. The present invention encompasses the use of many α-fucans, and in particular the fucans present in many sea plants (such as seaweed) and sea vegetables, such as the sea cucumber body wall; in particular the α-fucan present in the cell walls of marine brown algae, and the egg jelly coat of sea urchin eggs. Ideally the present invention utilises fucoidan, the α-fucan present in brown seaweed.

Preferably, the composition contains a high proportion of β-glucans and/or α-fucans and natural minerals and a corresponding low proportion of alginate and polyphenols. In some preferred aspects of the invention, the prebiotic composition comprises a mixture of at least about 8% by weight β-glucans and at least about 8% α-fucans. Preferably, the composition comprises between about 8% and 30% β-glucans and between about 8% and about 30% α-fucans. The combined amount of β-glucans and α-fucans may be up to about 60% (w/w) of the said composition; preferably the β-glucans and/or α-fucans are present in a combined amount of between about 20% to about 30% of the composition. Some embodiments of the invention may provide different ratios depending on the intended usage, for example, some embodiments may provide increased α-fucan proportion to provide increased effect as an antibiotic substitution. Other applications of non-equal ratios will be readily apparent to the skilled person, taking into account the different relative qualities of β-glucans and α-fucans and the intended usage thereof.

The compositions of the invention may further comprise mannitol. While not wishing to be bound by theory, it is believe that mannitol when used in combination with one or both of β-glucans and α-fucans, provides a co-operative effect to increase the overall efficacy; due in part to mannitol increasing the sweetness of the feed supplement or mannitol aiding the translocation of minerals and/or trace elements in the digestive tract due to its smaller molecular size. Preferably, mannitol is present in an amount of between about 5% and about 25% (w/w) of the composition. In addition, lactose (pure or as whey) may be also be provided with the compositions of the invention. Preferably, lactose is present in an amount of between about 5% and about 30% (w/w) of the composition. The composition may also further comprise minerals and trace elements. The levels of minerals can be from 5 to 40% depending on the application. Favourably, the compositions of the invention may be used in combination with animal feed. Ideally, the compositions of the invention may be used in combination with animal feed in an amount of about 0.1 to about 10% by weight. In alternate embodiments, the animal feed may also contain up to 30% of lactose. The lactose can act synergistically with the other components of the composition.

In preferred embodiments, the β-glucans and/or α-fucans are derived from natural materials such as seaweed, barley, mushrooms, oats, yeast and other microbial sources. The seaweed may be one or more selected from the group consisting of *Laminariaceae, Fucacea, Gigartinaceae, Ascophyllum, Laminaria, Durvillea, Macrocystis, Chondrus* and *Eclclonia*. Particularly preferred are *Laminaria* and/or *Ascophyllum*. The β-glucans and/or α-fucans may be derived from more than one source. Other components of the invention may be derived from the same or alternative sources.

The composition may be provided in a powder form. The total solid content may be above about 90% of the total weight. The following are examples of ideal ranges by weight of some of the typical constituents of the composition: total ash content may be below about 40%; total protein content may be in the range of about 3 to about 7%; the total fat content may be about 4%; total carbohydrate content may be about 50%; reducing sugar content may be in the range of about 1 to about 5%; total concentration of β-glucans and/or α-fucans may be about 20% to about 25%; Insoluble (non-dietary) fibre content may be in the range of about 2 to about 6%; methylpentosan content may be in the range of about 2 to about 6%; total phenol content may be below about 5%, and ideally below 2%; total content of antioxidants (including BHA, BHT, Ethoxyquin, Vitamin C, Tocopherols) may be up to about 5%, total content of alginate may be less than about 5% and ideally less than about 2%.

The composition may also contain contains trace (less than about 500 ppm) amounts of plant growth hormones like Cytokinins, Auxins, Gibberellin and Betaines; The prebiotic composition may also contain an appropriate amount of a low pH food grade preservative, such as sodium benzoate, although a huge variety of food preservatives would be suitable.

In alternative embodiments of the invention, the prebiotic composition may be provided in a liquid form such that it contains about 10 to about 50% (w/v) of the powder as previously described. The liquid extract may then be spray dried to obtain an extract in powder form, which may, for example, be cream-coloured.

The invention may also be provided in the form of an animal feed composition comprising animal feed and the prebiotic composition of the invention, wherein said composition is present at about 0.001 to about 10% by weight, said amount being sufficient to effect prebiotic action and pH lowering action in an animal and which is orally administered as part of said animal feed composition. The animal feed compositions and/or prebiotic compositions of the invention may be administered independently to the animals or along with a carrier selected from a group consisting of but not limited to water, oil, milk and mixtures thereof.

The prebiotic composition may be mixed together with one or more probiotic cultures, suitably as a tablet or a capsule. Some embodiments may contain over 10% or more probiotic culture, while in other embodiments, the ratio of prebiotic to probiotic culture is 1:3 A broad range of probiotic cultures may be suitable for use in the various embodiments of the invention, such as *Bifidobacteria Lactobacilli, leichmannii, L. plantarum, L. cellobiosius, B. adolescentis* and/or *L. acidophilus*. In preferable embodiments the probiotic culture is a *Lactobacilli* or *Bifidobacteria*.

The invention also provides for a pharmaceutical preparation comprising a suitable pharmaceutical carrier and one or more of the compositions of the present invention.

The invention also relates to a method of obtaining such a composition from seaweed consisting of a novel acid extraction step combined with a nanofiltration step. The inventors have found that subjecting the acid extract of seaweed such as *laminaria* spp to a nanofiltration step results in a clear separation of the salts and results in light green liquid which can be dried into a cream colored powder which is ideal for the purposes of this invention. The liquid may also be used independently. This additional step of combining an acid extraction step with a nanofiltration step is novel. A further aspect of the invention is a method for the extraction of β-glucans, α-fucans and mannitol from seaweed. The seaweed may be of different species, for example: *Ascophyllum nodosum, Fucus, Laminaria digitata, Laminaria saccharina, Laminaria hyperborea*.

The invention provides a process for obtaining a composition from seaweed comprising;
(i) Maintaining the temperature of a seaweed solution at about 50° C. to about 80° C.;
(ii) Maintaining the pH of the solution at acidic pH;
(iii) Decanting the solution;
(iv) Clarifying the solution; to yield a clarified seaweed extract.

On the process side, most researchers in the field have focused on the extraction of pure (3-(1,3) (1,6) glucans in their native conformational state as this is necessary for them to exhibit their immunological action. The 3-glucans from yeast have been shown to exert immunological effects in humans and animals and most patents in the space have focused on extracting such glucans, usually in a microparticulate form, and then solubilizing them to render them safe for an intravenous application. Water solubility is achieved either through the cleavage of the large microparticulate glucan form to smaller molecules using processes such as enzymatic digestion or vigorous pH adjustments, or by complexing to salts such as amines (U.S. Pat. No. 4,761, 042), sulphates and phosphates (U.S. Pat. No. 4,739,046). The principal advantage of the smaller, water soluble form vs. the larger microparticulate form is that it is safer when given by parenteral routes of administration, such as intravenously. Also, it is more likely that the smaller size molecules are more bio-available on a molar basis.

A process for the extraction of immunologically active glucans is described in various papers including Freimund et al (2003) who use an enzymatic process for the extraction of pure soluble β-glucans and Muller et al (1997), who have studied the influence of various protic acids used in extraction on the integrity and biological activity of the extracted glucans. Similarly U.S. Pat. Nos. 5,633,369 and 5,705,184, US 2004008253, US 20020143174 (very high molecular weight glucans) and US 20020032170 discuss a process for producing soluble glucans with a direct biological activity from yeasts. A subset of any of these processes can be used to make, for example, the β-(1,3) (1,6) glucans from yeast for some favourable aspects of the present invention. In the present invention, it is not essential to separate the cell wall manno-proteins and lipids, as these may have beneficial biological effects of their own when applied to animals.

The present invention is a significant improvement over developments disclosed in the prior art. Known acid extraction methods, for example GB 727,013, are known to be somewhat uneconomical as a relatively low yield of nutrients is obtained. Primarily for this reason, the tendency has been to use an alkali extraction process as these typically obtain higher nutrient yields than previously known acid extraction methods. However, research has shown that, surprisingly, using alkaline extracted seaweed extracts resulted in a tendency to reduce weight gain in test animals (Pierce, A, 2002).

Thus, there was a need for an acid extraction process that could be carried out economically at a large scale and gave yields that were commercially viable. The above process is such an extraction process and can be used to produce the composition on a large scale.

Gore Vivian et al in U.S. Pat. Nos. 6,342,242, 6,432,443, 6,338,856, 6,312,709, 6,270,812, 6,383,538, 6,391,331 and US 20030003134 and US 20020022049 refer to the use of seaweed extract from *Ascophyllum nodosum* and meal in animal diet. The seaweed was found to enhance immune response in mammals and poultry, reduce *E. coli* content in beef and improve the shelf life of the carcass. These documents teach a seaweed extract obtained by alkali hydrolysis. This alkali method of extraction provides a higher proportion of total nutrients, although a low proportion of 3-glucans; of no more than 8% and typically 6%-7.5%, and α-fucans; typically of 6%-8%, although yields of up to 9% are potentially possible. Alkaline extracts will typically include 25% Alginate and 7% polyphenols. The acid extraction methods of the present invention yield 80% less alginates and polyphenols than normal alkali extractions, for example, producing up to about 5% alginates and up to about 1-2% polyphenols. In contrast, the present invention provides particular components of the seaweed extract (α-fucans and/or β-glucans), derived by novel extraction processes that are beneficial to animal and human health. Furthermore, the mode of action prescribed in those documents, i.e. through a stimulation of the immune system is quite different from the mode of action of our composition, which acts as a prebiotic in large mammals and an anti-microbial in young mammals.

Potential Benefits of the Composition

The inventors have surprisingly found that the present invention provides compositions and methods that have a number of uses. The compositions of the invention can act as a prebiotic, i.e. to selectively act as a substrate for, and boost the growth of beneficial microbes like *bifidobacteria* in large mammals. In particular, compositions comprising β-(1,3)(1,6) glucans, (for example, those derived from yeast or seaweeds) are suitable with compositions comprising β-(1,3)(1,6) glucans derived from seaweed being particularly favourable. This effect is enhanced when the glucans are fed in combination with fucoidan and mannitol.

The beneficial bacteria, through competitive exclusion and through the secretion of specific metabolites (bacteriocins), reduce the growth of harmful bacteria like *E. coli* and *Salmonella*. Thus, the invention also provides methods of reducing the growth of harmful bacteria in mammalian intestines. The composition also has a direct anti-microbial action in young mammals, whose digestive systems may not be developed to break the constituents down into a prebiotic form. In this way, the composition acts as an excellent replacement to in-feed antibiotics and enhances animal performance to match and even exceed the effects of those antibiotics.

The compositions of the invention also provide a means for acidification of the large intestine which is beneficial to the animals and farming efficiency in the absence of in-feed antibiotic growth promoters. This lowering of the pH reduces the growth of harmful microbes like *E. coli* and enhances the prebiotic action of these carbohydrates. Compositions of the invention may be used as replacements for in-feed antibiotics. Another aspect of the present invention provides a synbiotic for humans or animals to restore helpful bacteria and boost their growth in the gut.

In addition, one of the components of this composition, fucoidan (α-fucan), has been reported to have anti-carcinogenic, anti-thrombatic and anti-viral effects in humans further boosting the utility of the composition.

The invention provides a method of improving gut health in humans or animals comprising treating the human or animal with one of more compositions of the invention, and in particular, the β-(1,3)(1,6) glucans from yeast, plant, fungal, microbial and algal sources. Traditionally, NSPs, particularly insoluble NSPs, have been implicated in reduced performance and digestibility. This is because high levels of NSPs in the diet increase the size of the gut (particularly the length of the long intestine) which places a bigger energy demand on the animal. However, if the compositions of the invention are administered separately in the dose recommended, they actually improve performance. Overall, a specific composition of algal polysaccharides, particularly laminarin and fuocidan have beneficial effects on pig performance as measured by food intakes, daily gain and feed conversion ratios. The invention provides for the use of algal polysaccharides, particularly laminarin and fuocidan, in feed supplements, as there will have beneficial effects on pig performance as measured by growth rates, daily gain and feed conversion ratios. These effects will vary depending on the algal source and the solubilities of the resulting polysaccharides.

The invention also provides methods of improving nutrient digestibility in large animals or humans comprising feeding the animals or humans compositions of the invention. In particular 3-(1,3) (1,6) glucans from yeast, fungal, microbial, plant or algal sources will improve nutrient digestibility in mammals. These will also improve the absorption of minerals and micronutrients by mammals. This is due to an improved gut structure (greater area for absorption of nutrients), and the increase of lactic acid producing bacteria particularly in large mammals.

Overall, the uses of the invention in general favour the use of the β-glucans derived from seaweed, as these are smaller and more soluble than even the β-glucans derived from yeast. Naturally, where uses and methods described herein relate to compositions of the invention, such compositions also relate to pharmaceutical preparations and feedstuffs.

Aspects of the invention also provide for the use of a composition comprising one or more of the compositions of the invention for one or more of the group consisting of: improving gut health in humans or animals, promoting the growth of beneficial bacteria in human or animal intestines, reducing the levels of harmful microbes like *E. coli* and *Salmonella* in animal or human intestines, improving animal performance and acting as a replacement for in-feed antibiotics and improving mineral absorption and nutrient digestibility.

Further aspects provide for the use of a composition comprising β-glucans and/or α-fucans in the preparation of a medicament for the treatment of one or more of the group consisting of gut inflammation and gut infection.

A pharmaceutical preparation comprising one or more of the above described compositions and a suitable pharmaceutical carrier. Suitable carriers are well known in the art and include liposomes, emulsions, surfactants, vegetable oils, totally or partially hydrogenated vegetable oils, lecithins, plant phosphatides and natural waxes. soya oil, totally or partially hydrogenated soya oil, rapeseed oil, ground nut oil, soya lecithin, soya phosphatides, egg lecithin and beeswax. The pharmaceutical preparation may also further include one or more selected from the group consisting of an enteric coating, L- and or D-amino-acids, vitamins, trace elements, natural oils, antioxidants, salts and solvents.

BRIEF DESCRIPTION OF THE DRAWINGS

For a more complete understanding of the features and advantages of the present invention, reference is now made to the detailed description of the invention along with the accompanying figures and in which:

FIG. 1 is a table, designated as Table 1, which represents the composition and chemical analysis of starter diets.

FIG. 2 is a table, designated as Table 2, which represents the effect of dietary treatment on faecal DM, faecal pH, faecal score, apparent digestibility coefficients and digestible energy content of start diets.

FIG. 3 is a table, designated as Table 3, which represents Composition and chemical analysis of starter diets (as fed).

FIG. 4 is a table, designated as Table 4, which represents effect of lactose level and GutCare concentration on pig performance after weaning (day 0).

FIG. 5 is a table, designated as Table 5, which represents the effect of GutCare on selected microbial populations in the caecum and colon of the piglet.

FIG. 6 is a table, designated as Table 6, which represents the composition and analysis of experimental diets.

FIG. 7 is a table, designated as Table 7, which represents the effect of GutCare concentration on microbial ecology in the colon.

FIG. 8 is a table, designated as Table 8, which represents the effect of GutCare concentration on total tract digestibility coefficients.

FIG. 9 is a table, designated as Table 9, which represents the effects of dietary treatment on faecal dry matter (DM), faecal pH and faecal score in piglets.

EXAMPLES

Example 1

Production of the Composition 5000 kg of the Raw material (*Ascophyllum nodosum*, but raw material could be any seaweed selected from the group mentioned above) in a wet state was washed, milled to approximately 10 mm and washed again. 5000 L of Water was added to a 15,000 L vessel and heated to 80° C. Ten litres of 36% Hydrochloric acid was added followed by the addition of the milled weed. The temperature was adjusted to between 75-80° C. by the addition of live steam and the pH adjusted to pH 4 with additional HCl. The vessel was then agitated for three hours followed by cooling to 50 degrees. The mixture in the vessel was then pumped to a press. The solids retained in the press were recycled and the procedure described above was repeated. The liquid from the press was then clarified, evaporated, and spray dried. A cream coloured product with the following composition was obtained.

1. Total Solids. 96.335% weight.
2. Ash Content. 33.210% weight.
3. Total Protein Content. 5.775% weight.
4. Total Fat Content. 2.876% weight.
5. Total Phenols. 37.500 mg/Kg.
6. Total Alginate Content. <5%
7. Laminarin Content. 9.850% weight.
8. Total Mannitol. 4.175% weight.
9. Fucoidin Content. 12.936% weight.
10. Total Carbohydrate Content. 59.335% weight.
11. Reducing Sugars Content. 3.500% weight.
12. Fibre Content. 4.580% weight.
13. Methypentosans. 4.775% weight
14. Antioxidant Analysis
    BHA 3.558 mg/Kg
    BHT 5.195 mg/Kg
    Ethoxyquin 1.886 mg/Kg
    Vitamin C 14.505 mg/Kg
    Tocopherols Vitamin E 2 mg/mg/Kg
15. Growth Hormones
    Cytokinin Content. 16.500 ppm.
    Auxin Content. 10.176 ppm.
    Gibberellin Content. 5.800 ppm.
    Betaine Content. 26.555 ppm.

A small amount of a food-grade preservative, sodium benzoate was also added to the above composition to maintain the integrity of the composition, hereinafter called GutCare. GutCare is a trademark.

Example 2

Digestibility

Experimental Diets

The experiment was designed as a 3×2 factorial (3 lactose levels×2 GutCare levels) consisting of 6 dietary treatments. The treatments were as follows (T1) 65 g/kg lactose with no supplementation, (T2) 170 g/kg lactose with no supplementation, (T3) 275 g/kg lactose with no supplementation, (T4) 65 g/kg lactose+5 g/kg GutCare, (T5) 170 g/kg lactose+5 g/kg GutCare and (T6) 275 g/kg lactose+5 g/kg GutCare. The starter diets were fed in meal form for 27 days. The compositions and chemical analysis of the experimental diets are shown in Table 1. The diets were formulated to have identical digestible energy (16 MJ/kg) and total lysine (16 g/kg) contents by adjusting soya oil and synthetic amino acids. Amino acid requirements were met relative to lysine (Close, 1994). All diets were milled on site. Chromic oxide ($Cr_2O_3$) was added to the diet during milling at a concentration of 150 ppm to determine nutrient digestibility.

Animals & Management 165 piglets (progeny of Large White×(Large White×Landrace sows)) were weaned at 24 days of age and had an initial live weight of 5.90 kg. The piglets were blocked on the basis of live weight and within each block were randomly assigned to one of six dietary treatments. The pigs were housed on fully slatted pens (1.68 m×1.22 m). There were six replicates/treatment. Temperatures of the houses were kept at 30° C. during the first week and were then reduced by 2° C. per week. Each pig was weighed initially and on day 8, day 15, day 21 and day 27. The pigs were fed ad libitum and care was taken to avoid any wastage. Feed was available up to weighing but after weighing all the remaining feed in the trough was weighed back. Throughout the experiment samples of the feed were taken for chemical analysis. Fresh fecal samples were collected from each pen on a daily basis from days 10-14 to measure digestibilities. Feces samples were also collected from each pen every second week to measure fecal pH.

Feces Scoring

The pigs were closely monitored for any signs of diarrhea and a scoring system was used to indicate the presence and severity of this. Feces scoring was carried out on Day 0 and continued up until day 27. The feces scoring applied was: 1=watery like feces, 2=semi-liquid feces, 3=soft but partially solid feces, 4=slightly soft feces, 5=solid feces.

Laboratory Analysis

Both concentrates and feces were analysed for nitrogen, dry matter, ash, gross energy, neutral detergent fibre and chromium concentration. After collection, the feces were dried at 100° C. for 72 hours. The concentrates and dried feces were then milled through a 1-mm screen (Christy and Norris hammer mill). The dry matter was determined after drying overnight (min 16 hours) at 103° C. Ash was determined after ignition of a known weight in a muffle furnace (Nabertherm, Bremen, Germany) at 550° for 4 hours. Crude protein was determined as Kjeldahl Nx6.25 using both a Buchi 323 distillation unit and a Buchi 435 digestion unit (Buchi, Flawil/Schweiz, Switzerland) according to AOAC (1980). Neutral detergent fibre and crude fibre was determined using a Fibertec extraction unit (Tecator, Hoganans, Sweden). The Neutral detergent fibre was determined according to Van Soest (1976).

Gross energy of both the feed and fecal samples was determined using a Parr 1201 oxygen bomb calorimeter (Parr, Moline, Ill., USA). The chromium concentration was determined according to Williams et al. (1962).

Statistical Analysis

The experimental data was analysed as a 3×2 factorial using the General Linear Model procedure of Statistical Analysis System Institute (1985). The models for performance and digestibility analysis included the main effects of lactose level, the composition of the invention or GutCare and the interaction between lactose level and the composition of the invention or GutCare. Initial liveweight at weaning was included as a covariate in the model.

Results

Nutrient Digestibility & Fecal Analysis

The effects of dietary treatment on fecal DM, fecal pH, fecal score and apparent nutrient digestibilities of the diets are presented in Table 2. Pigs offered diets containing GutCare had harder feces between days 15-21 than pigs offered diets without GutCare. There was a significant interaction between lactose level and GutCare for feces score during days 15-21. Pigs offered diets containing 275 g/kg lactose with GutCare had softer feces compared to pigs offered diets containing 275 g/kg without GutCare. This is probably due to the overloading effect of excess carbohydrates in the lower gut. Pigs offered diets containing GutCare had solider feces between days 21-27 than pigs offered diets without GutCare. Pigs offered diets containing GutCare had a significantly lower feces pH compared to pigs offered diets without GutCare. There was a significant interaction between lactose level and GutCare in dry matter (DMD) ($P<0.01$), organic matter (OMD) ($P<0.01$), neutral detergent fibre (NDF) ($P<0.05$), nitrogen ($P<0.001$) and gross energy (GE) ($P<0.001$) digestibilities. The inclusion of GutCare extract to 275 g/kg lactose significantly reduced apparent nutrient digestibilities of DMD, OMD, NDF nitrogen and gross energy compared to pigs offered 275 g/kg lactose without GutCare. However, the inclusion of GutCare to 65 g/kg lactose significantly improved apparent nutrient digestibilities of DMD, OMD, NDF, nitrogen and digestible energy compared to pigs offered 65 g/kg lactose without GutCare.

Discussion of Example 2

The results show that the inclusion of GutCare reduces the requirement for high lactose in antibiotic free piglet diets, and improve digestibility in low lactose diets. There was a significant interaction between lactose and GutCare in DMD, NDF, OMD, nitrogen and GE digestibility. The pigs offered the low level of lactose with the GutCare had significant improvements in DMD, NDF, OMD, nitrogen and digestible digestibility of 0.02, 0.06, 0.02, 0.03 and 0.03 respectively compared with pigs offered diets containing the low level of lactose without GtCare.

However, the inclusion of GutCare to the high lactose diets resulted in a decrease in DMD, NDF, OMD, nitrogen and GE digestibility of 0.02, 0.12, 0.02, 0.05 and 0.03 respectively compared to the high lactose diet unsupplemented with GutCare. The combination of the high lactose and GutCare resulted in an excessive quantity of carbohydrate entering the colon that exceeded the fermentation capacity of the piglet. Mul and Perry (1994) showed that an excess intake of oligosaccharides can result in excessive fermentation which may lead to undesirable conditions in the large intestine.

The significant interaction between lactose level and GutCare in fecal consistency when pigs were offered diets containing the high level of lactose supplemented with GutCare resulted in softer feces than pigs offered diets containing the high level of lactose unsupplemented with GutCare indicating such an overload.

The inclusion of GutCare to the low, medium and high lactose diets resulted in a significant reduction in fecal pH. This lowering of the pH is due to the increased production of VFAs in the hind gut and indicates a prebiotic effect for GutCare.

In conclusion, the inclusion of the GutCare to the low lactose diets improved nutrient digestibility however, the inclusion of GutCare to the high lactose diets reduced nutrient digestibility due to an overloading of the gut as described above. However, the inclusion of GutCare in the diet lowered the pH of the feces, indicating a prebiotic effect.

Example 3

A process for producing the composition from algae comprises the following:

1) Washing the sand and grit off the wet weed, chopping the wet weed to pieces, about 3 to about 10 mm followed by sand separation.

2) Extracting the chopped weed in water at a temperature ideally between about 70-80 deg C. for about 2-3 hours at a pH of about 3.5 to about 4.5 and preferably about pH 4. The seaweed is preferably combined with water. The water may be brought to, or is at, a temperature between about 0° C. to about 100° C., preferably between about 37° C. and 95° C., more preferably about 50° C. to about 80° C., and most preferably about 75° C.

The process of the invention is ideally carried out at pH 1 to pH 7, more preferably pH 1 to pH 6, more preferably about pH 4 to about pH 5 and most preferably about pH 4.5. In one embodiment the pH of the solution can be adjusted to about pH 4.5 prior to the agitation step. While not wishing to be bound by theory, it is believed that a pH between about pH 4 and about pH 5 optimises yield, while lowering the requirement for addition of acids, minimising the hydrolysis effects and harm thereof. Ideally, the acid used is chosen from a group consisting of inorganic acids like hydrochloric acid, phosphoric acid and sulphuric acid and organic acids like lactic acid, formic acid and propionic acid, or any soluble inorganic or organic acid.

3) The process of extraction is further aided by continuous agitation. Ideally, the mixture is agitated for a period of time, preferably between about 1-10 hours, and most preferably about 3 hours. The agitation creates a slurry.

4) The processed material can then be cooled to 10-50° C. thus protecting sensitive compounds and/or making the material safe to press.

5) Ideally, the mixture may then be decanted or pressed.

6) The insoluble material may be collected and reprocessed using the same procedure outlined above.

7) The liquid plus small insoluble residue is pumped to a clarifier where the remaining insoluble fractions are removed. The product may be clarified to yield a liquid composition.

8) The clarified liquid can be pumped to a storage tank (direct to nanofiltration unit or evaporator) from where it can be pumped to evaporator for concentration or to nanofiltration (NF) plant where up to 70% of the chloride salts are removed and up to 30% of the sodium and potassium salts are removed. This desalting helps to remove the salty taste in the product. The operating pressure in the NF step is between 20-40 bar and preferably 25 bar and the membrane pore size is $10^{-3}$-$10^{-2}$ um.

9) If the application requires a high degree of desalination the product can be processed by either Electrodialysis or Ion Exchange.

10) The concentrated, nanofiltered or demineralised product can be evaporated and a preservative such as sodium benzoate added if required in liquid form.

11) As a further embodiment to make a purified β-glucan & α-fucan evaporated product, the product can be crystalised in crystallation tanks where the mannitol is converted to crystals and removed by centrifugation. This involves obtaining a highly concentrated liquid, followed by transfer to crystallation tanks, followed by seeding, followed by cooling at a predetermined time and temperature. When the crystals are formed the product is then centrifuged is a two step separation process separating the crystals for drying in a fluid bed dryer and the balance of the product which is high in β-glucans and α-fucans available to be dried in a spray dryer.

12) The evaporated product can be dried in a spray dryer. The resultant powder is a cream colour.

13) Solubilisation of the laminarin may be required if the starting raw material is *Laminaria hyperborea*. In this case the product after clarification is subjected to pH modification as per the process described for yeast glucans in US Pat. No 20040082539.

Example 4

Performance

Diets

The experiment was arranged as a 4×3 factorial (4 GutCare levels and 3 lactose levels), over four consecutive runs. 384 piglets (progeny of Large White×(Large White×Landrace)) were selected after weaning at 21 days with an initial live weight of 7.43 kg. The pigs in run 1, 2, 3 and 4 had an initial live weight of 7.88 kg, 7.57 kg, 6.56 kg and 7.72 kg respectively. The pigs were blocked on the basis of live weight and within each block assigned to one of twelve dietary treatments. The dietary treatments consisted of (T1) 24.3 g/kg lactose with 0 g/kg GutCare, (T2) 24.3 g/kg lactose with 3 g/kg GutCare, (T3) 24.3 g/kg lactose with 6 g/kg GutCare (T4) 24.3 g/kg lactose with 12 g/kg GutCare, (T5) 15.3 g/kg lactose with 0 g/kg GutCare, (T6) 15.3 g/kg lactose with 3 g/kg GutCare. (T7) 15.3 g/kg lactose with 6 g/kg GutCare. (T8) 15.3 g/kg lactose with 12 g/kg GutCare. (T9) 6.3 g/kg lactose with 0 g/kg GutCare. (T10) 6.3 g/kg lactose with 3 g/kg GutCare. (T11) 6.3 g/kg lactose with 6 g/kg GutCare. (T12) 6.3 g/kg lactose with 12 g/kg GutCare. The starter diets were milled on site and offered in meal form for 21 days post weaning. Diets were formulated as described in Example 2 except chromium oxide was at a concentration of 200 p.p.m. The ingredient composition and chemical analysis of the dietary treatments are presented in Table 3. The composition of the invention used in this example was a liquid sample with 33% solids.

Management

Pigs were housed in groups of four (eight replicates per treatment) as described in Example 2. Pigs were weighed initially and on days 7, 14 and 21. Fresh fecal samples were collected once daily from all pens on days 10 to 15.

Statistical Analysis

The experimental data were analysed as a 4×3 factorial as described in Example 2

Results
Performance

The effects of lactose level and GutCare concentration on average daily gain (ADG), food intake and food conversion ratio (FCR) are presented in Table 4. There was a significant interaction between lactose and GutCare (P<0.05) on average daily gain (ADG) between days 0-7. Pigs offered diets containing no GutCare supplementation and low lactose levels had lower ADGs than pigs offered diets containing GutCare and high lactose. There was significant lactose by GutCare interaction on ADG in the overall growing period (days 0-21). Pigs offered diets containing GutCare and low lactose levels had lower ADGs than pigs offered diets containing GutCare and high lactose. GutCare also had a significant independent linear effect on daily gain (P<0.01) and led to an improvement in daily gain, at all lactose levels.

There was a significant interaction between lactose and GutCare (P<0.05) during the starter period (days 0-7) on average daily feed intake (ADFI). Pigs offered high lactose diets and 3 g/kg GutCare had the overall highest ADFI. The inclusion of 6 g/kg and 12 g/kg GutCare at the high levels of lactose decreased ADFI. However, pigs offered medium levels of lactose and 12 g/kg GutCare and pigs offered low lactose diets and 6 g/kg GutCare obtained higher ADFIs than the pigs offered the same levels of lactose but no GutCare.

There was also a linear increase in ADFI (P<0.05) as the level of GutCare increased between days 7-14 and again between days 14-21. There was a linear increase to both lactose level (P<0.05) and GutCare supplementation (P<0.05) on ADFI during the overall starter period (0-21) as the level of both increased.

There was a significant interaction between lactose and GutCare (P<0.05) on food conversion ratio (FCR) during days 0-7. There was an improvement in FCR as the level of GutCare increased at both medium and low lactose level. However, at medium levels of lactose there was an improvement in FCR up to 6 g/kg GutCare where there was deterioration thereafter. There was a linear decrease (P<0.05) in FCR, representative of improved feed efficiency, during the overall starter period (days 0-21) as the level of GutCare increased. Likewise there was also a tendency of a significant lactose by GutCare interaction (P<0.09) during days 0-21. Overall GutCare improved the feed conversion ratio in most of the diets. Furthermore, GutCare also led to more solid feces, particularly during day 0-7 as shown in Table 9.

There was also a numerical tendency (p=0.13) for a drop in fecal pH on addition of GutCare at low lactose levels, indicating a prebiotic effect.

Discussion

The above experiments show the benefit of GutCare on animal performance in the absence of in feed antibiotics. The effect is as strong as the effect of the antibiotics the formulation is meant to replace. There is an improvement in daily gain, intake as well as feed conversion ratio, which are the key performance parameters. The composition interacts with lactose, which is to be expected, as both consist primarily of carbohydrate components, and giving an excess of the two could result in an overloading effect on the digestive system. This is discussed in greater detail in Example 2. GutCare works best at low and medium levels of lactose, providing an effective means to reduce the level of lactose (an expensive component) needed in animal diets. The harder feces as observed in Day 0-7 are representative of a reduction in scouring, which is a key health parameter in young piglets, which are especially susceptible to diarrhea.

Experiment 5
Anti-Microbial
Animals and Experimental Diets

The experiment was designed as a 2×1 factorial. Ten piglets (progeny of Large White×(Large White×Landrace)) were selected from four closely related sows at 24 days of age. The piglets had a weaning weight of 7.8 (s.d 0.83) kg. They were blocked on the basis of litter, weight and sex and within each block randomly assigned to one of two dietary treatments. The dietary treatments were as follows: T1) Standard Diet; T2) Standard Diet+1.8 g/kg GutCare. Diets were formulated as described in Experiment 2.

Management

The pigs were housed individually as described in Experiment 2.

Microbiology

The effect of GutCare on selected microbial populations in the caecum and colon are shown in Table 5. GutCare had a significant effect on the microbial populations in the caecum with a decrease in the *E. coli* (P<0.01), *Bifidobacteria* (P<0.05), and *Lactobacilli* (P<0.05) populations. GutCare had a significant effect on the *E. coli* population (P<0.01) and the *Lactobacilli* population (P<0.001) of the colon, causing a decline.

Discussion

The composition has a pronounced anti-microbial action, similar to in-feed antibiotics in piglets. This is beneficial from a performance perspective, as a lower microbial load will result in a lower energy cost to the pig. Also, the removal of harmful bacteria like *E. coli* helps control disease rates in piglets.

As mentioned above, the composition plays a role similar to the antibiotics in small pigs, acting as a replacement for them. This behaviour is different to the behaviour in large pigs where the formulation plays more of a prebiotic role. The reason for the difference could be the inability of the small pigs to break down some of the components in the composition to a form in which they act as a prebiotic. This is in line with the objectives of the formulation to act as a substitute for antibiotics in the small pig.

Example 6

Prebiotic and Mineral Absorption

Experimental Design and Diets

The experiment was designed as a complete randomised design comprising of five dietary treatments. All diets were formulated to have identical concentrations of net energy (9.8 MJ/kg) and total lysine (10.0 g/kg). The amino acid requirements were met relative to lysine (Close, 1994). All diets were fed in meal form. GutCare was supplied by BioAtlantis Ltd. (Kerry Technology Park, Tralee, Ireland). The dietary composition and analysis are presented in Table 6.

The experimental treatments were as follows:
(1) 0 g/kg GutCare (control)
(2) 0.7 g/kg GutCare
(3) 1.4 g/kg GutCare
(4) 2.8 g/kg GutCare
(5) 5.6 g/kg GutCare Animals and Management Sixteen finishing boars progeny of Meat line boars× (Large White×Landrace sow)) with an initial live weight of 51 kg (s.d=3.4 kg) were used in this experiment. The pigs were blocked on the basis of live weight and were randomly allocated to one of five dietary treatments. The pigs were allowed a 14-day dietary adaptation period after which time they were weighed and transferred to individual metabolism crates. The pigs were given a further 5 days to adapt to the metabolism crates before collections began. The collection period was sub-divided into two parts to facilitate studies on apparent digestibility (days 3 to 7). The daily feed allowance (DE intake=3.44×(live weight) 0.54 (Close, 1994) was divided over two meals. Water was provided with meals in a 1:1 ratio. Between meals, fresh water was provided ad libitum. The metabolism crates were located in an environmentally controlled room, maintained at a constant temperature of 22° C. (±1.5° C.).

Apparent Digestibility Study

During collections, urine was collected in a plastic container, via a funnel below the crate, containing 20 ml of sulphuric acid (25% $H_2SO_4$). The urine volume was recorded daily and a 50 ml sample was collected and frozen for laboratory analysis. Total feces weight was recorded daily and oven dried at 100° C. At the end of the collection period, the feces samples were pooled and a sub-sample retained for laboratory analysis. Feed samples were collected each day and retained for chemical analysis.

Microbiology

All animals remained on their respective dietary treatments until slaughter. Digesta samples (approximately 10 g+1 g) were aseptically removed from the colon of each animal immediately after slaughter, stored in sterile containers (Sarstedt, Wexford, Ireland) on ice and transported to the laboratory within 7 h. *Bifidobacteria* spp. and *E. coli* were isolated and counted according to the method described by O'Connell et al., (2005). *Bifidobacteria* spp was chosen because of its positive effect on gut health while *E. coli* species was chosen because of its negative effect on gut health (De Lange, 2000).

Laboratory Analysis of Samples

Proximate analysis of diets for dry matter (DM) and ash was carried out according to Association of Analytical Chemists, (1980). The dry matter of the feed was determined after drying overnight at 103° C. Ash was determined after ignition of a known weight of concentrates or feces in a muffle furnace (Nabertherm, Bremen, Germany) at 500° C. for four hours. The gross energy (GE) of feed and feces samples was measured using an adiabatic bomb calorimeter (Parr Instruments, Il, USA).

Results

Microbiology Study

The effect of dietary treatment on selected microbial populations and pH in the colon are presented in Table 7.

There was a significant response to GutCare on colonic *E. coli* and colonic *bifidobacteria* populations (quadratic P<0.05). There was a significant (quadratic) decrease in *E. coli* population while there was an increase in *bifidobacteria* populations, up to a certain level. At high concentrations, these populations decreased, indicating overloading of the gut.

Total Tract Digestibility.

The effect of dietary treatment on ash total tract digestibility is presented in Table 8. There was a significant linear increase (P<0.01) in total tract ash digestibility with increasing extract concentration.

Discussion

This experiment shows the effect of GutCare on the gut microflora in growers and on mineral absorption (represented as ash digestibility). As can been seen from the results, the composition resulted in an increase in beneficial bacteria levels and a reduction in the levels of harmful microbes. This response is typical of prebiotic formulations. At higher dosages, the levels of all microbes changed, indicating overloading of the gut, again a response typical of prebiotic formulations. Furthermore, the increase in ash digestibility (which consists of micro and macro nutrients) indicates increased absorption of these nutrients in the gut.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

REFERENCES

Association of Analytical Chemists 1995. Official methods of Analysis, 16.sup.th edition, Association of Official Analytical Chemists, Washington D.C., USA.

Autio, K., Mannonen, I., Pierila, K., Kosinken, M., Siikaaho, M., Linko, M. 1996 Journal of the Institute of Brewing 102, 427-432.

Adams, C. A., 2001. In: Total Nutrition: Feeding animals for health and growth (ed. C. A. Adams), Nottingham University Press, Nottingham, United Kingdom, pp 157-161.

Bach Knudsen, K. E. 1991. In: Digestive Physiology in Pigs, Proceedings of the Vth international symposium on digestive physiology in pigs. (ed. M. W. A. Verstegen, J. Huisman and L. A. den Hartog) pp 428-434. Purdoc Wageningen, Wageningen, The Netherlands.

Bach Knudsen, K. E. and Hansen, I. 1991. British Journal of Nutrition 65: 217-232.

Bedford, M. R. 2000. Animal Feed Science and Technology 86: 1-13.

Bergh M. O., Razdan A. and Aman P Animal Feed Science and Technology 201 (1999) 215-226.

Brownlee I. A, Allen A, Pearson J. P., Dettmar P. W, Havler M. R., Atherton M. E, and Onsoyen E, 2005, Critical Reviews in Food Science and Nutrition, 45: 497-510

Burtin, P., 2003. Electronic Journal of Environmental Agriculture and Food Chemistry. Volume 2, Issue 4.

Campbell, G. L. and Bedford, M. R. 1992. Canadian Journal of Animal Science 72: 449-466.

Canh, T. T., Sutton, A. L., Aarnink, A. J. A., Verstegen, M. W. A., Schrama, J. W. and Bakker, G. C. M. 1998. Journal of Animal Science 76: 1887-1895.

Blonden C, Chaubet F, Nardella, A, Sinquin C, Jozefonvizc, J, Biomaterials, 17 (1996), 597-603, Charalampopulous, D., Wang, R., Pandiella, S. S, and Webb, C. 2002. International Journal of Food Microbiology 79:131-141.

Close, W. H., 2000. Advances in pork production 11:47-56.

Cole, D. J. A., Beal, R. M. and Luscombe, J. R., 1968. Veterinary Record 83: 459-464.

Cueno, R. P., Morillo, T. B., Carter, S. D., Lachmann, M. S., Park, J. S, and Schneider, J. D., 2004. www.ansi.ostate.edu/research/2004rr/32/32.htm Choct, M. 1997. Feed Milling International June 1997: 13-26.

Close, W. H. 1994. In: Principals of Pig Science pp 123-140. (ed. D. J. A. Cole, J. Wiseman and M. A. Varley), Nottingham University Press, UK.

Conway, E. J. 1957. Microdiffusion Analysis and Volumetric Error. Crosby Lockwood and Son, London, 465 pps.

Cui, W., Wood, P. J., Blackwell, B., & Niliforuk, J. (2000). Carbohydrate Polymers, 41(3), 249-258.

De Lange, C. F. M. 2000. In: feed evaluation—principals and practice (ed. P. J. Moughan, M. W. A. Verstegen and M. I. Visser-Reyneveld) pp 77-92. Wageningen Pers, Wageningen, The Netherlands.

Derikx, P. J. L. and Aarnink, A. J. A. 1993. In: Nitrogen Flow in Pig Production and Environmental Consequences (ed M. W. A. Verstegen, L. A. den Hartog, G. J. M. van Kempen and J. H. M. Metz) pp 344-349. EAAP Publication No. 69, Purdoc, Wageningen, The Netherlands.

Dierick, N. and Decuypere, J. 1996. Pig News Information 17, 41N-48N.

Drew, M. D., A. G. van Kessel, A. E. Estrada, E. D. Ekpe and R. T. Zijlstra. 2003. Canadian Journal of Animal Science 82:607-609.

Etheridge, R. D.; Seerley, R. W.; Wyatt, R. D., JOURNAL OF ANIMAL SCIENCE, Vol. 58, No. 6, 1984, 1396-1402

European Council, 2001. Commission regulation (EC) no. 418/2001 of 1 Mar. 2001 concerning the authorisation of new additives and uses of additives in feedingstuffs. Official Journal of the European Communities L 62, Feb. 1, 2001.

Gao, Y., Lackeyram, D., Rideout, T., Archbold, T., Duns, G., Fan, M. Z., Squires, E. J., De Lange, C. F. M. and Smith, T. K. 2001. In: Digestive Physiology in Pigs, Proceedings of the 8.sup.th symposium on digestive physiology in pigs, (ed. J. E. Lindberg and B. Ogle) pp 338-340. CAB International, Wallingford, UK.

Darcy-Vrillon, B., Vaugelade, P., Bernard, F., Hoebler, C., Guillon, F., Mabeau, S, and Duee, P-H., 1996 Reproduction Nutrition Development 36: 425.

De Mitchell, I., and R. Kenworthy. 1976. Journal of Applied Bacteriology 41:163-174.

Drochner, W., Kerler, A. and Zacharias, B., 2004 Journal of Animal Physiology and Animal Nutrition 88: 367-380.

Estrada, A., Drew, M. D. and Van Kessel., 2001. Canadian Journal of Animal Science 81:141-148.

Freimund S, Sauter M, Kappeli O, Dutler H, Carbohydrate Polymers 54 (2003) 159-171.

Gibson, G. R. and Roberfroid, M. B., 1995. Journal of Nutrition 125: 1401-1412.

Glisto, L. V., Brunsgaard, G., Hojsgaard, S., Sandstrom, B. and Bach Knudsen, K. E., 1998 British Journal of Nutrition 80: 457-468.

Gray, J., 2003. Carbohydrates: Nutritional and health aspects. International Life Science Institute. Jan. 1, 2003, ISBN 1-57881-146-5.

Graham, H. and Pettersson, D. 1992. Swedish Journal of Agricultural Research, 22: 39-42.

Havenaar R, Huis In't Veld M J H. Probiotics: a general view. In: Lactic acid bacteria in health and disease. Vol 1. Amsterdam: Elsevier Applied Science Publishers, 1992.

Hayes, E. T., Leek, A. B. G., Curren, T. P., Dodd, V. A., Carton, O. T., Beattie, V. E. and O'Doherty, J. V., 2004. Bioresource Technology 91: 309-315.

Hobbs, P. J., Misslebrook, T. H. and Pain, B. F. 1995. Journal of Agricultural Engineering Research 60: 137-144.

Heo, S-J., Park, E-J., Lee, K-W. and Jeon, Y-J., 2005. Bioresource Technology 96: 1613-1623.

Hiss, S., Sauerwein, H., 2003. Journal of Animal Physiology and Animal Nutrition 87: 2-11.

Hogberg A and Lindberg J E, Animal Feed Science and Technology, 2005.

Houdijk, J. G. M., Bosch, M. W., Verstegen, M. W. A., Berenpas, H. J., 1998. Animal Feed Science and Technology 71: 35-48.

Ito, K. and Hori, K. 1989. Food Reviews International, 5, 101-144.

[0163] Itoh, Hiroko, et al., Anticancer Research, vol. 13, pp. 2045-2052 (1993).

[0164] Jamroz, D., Wiliczkiewicz, A., Skorupinska, J., 1992. J. Anim. Feed Sci. 1, 37_50.

Jamroz, D., Wiliczkiewicz, A., Orda, J., Skorupinska, J., 1996. Wien. Tierarztl. Mschr. 83, 165_177.

Jaskari, J., Salovaara, H., Mattilla-Sandholm, T. and Putanen, K. 1993. In: Proceedings of the 25.sup.th Nordic cereal congress, (ed T. Aalto-Kaarlehto and H. Salovaara) University of Helsinki, Helsinki, pp 242-244.

Jaskari, J., P. Kontula, A. Siitonen, H. Jousimeies-Somer, T. Mattila-Sandholm and K. Poutanen. 1998. Applied Microbiology Biotechnology 49:175-181.

Jensen, B. B. and H. Jorgensen. 1994. Applied Environ. Microbiol. 60:1897-1904

Kenworthy, R., and W. E. Crabb. 1963. Journal of Comparative Pathology 73:215-228.

Kim, I I., Jewell, D. E., Benevenga, N. J. and Grummer, R. H. 1978. Journal of Animal Science 46: 1658-1665.

Llaube'res, R. M., Richard, B., Lonvaud, A., Dubourdieu, D. and Fournet, B. (1990) Carbohydrate Research 203, 103-107.

Leek, A. B. G. 2003 Ph.D. Thesis, National University of Ireland, University College Dublin, Ireland Leek, A. B. G., Beattie, V. E., O'Doherty, J. V. 2004. Animal Science 79: 155-164.

Mabeau, S.; Kloareg, B. J. Exp. Bot. 1987, 38, 1573-1580.

Pereira, Mariana S., et al., J. Biol. Chem., vol. 274, No. 12, pp. 7656-7667 (1999).

MacGregor, A. W. a. B., & Rattan, S. (1993). Barley chemistry and technology. St. Paul, USA: American Association of Cereal Chemists Inc.

Mackie, R. I., Stroot, P. G. and Varel, V. H. 1998. Journal of Animal Science 76: 1331-1342.

Magnelli P, Cipollo J. F. and Abeijon C., Analytical Biochemistry, 301 (2002), 136-150.

Mahan, D. C., 1992. Journal of Animal Science 70: 2182-2187.

Mahan, D. C., 1993. Journal of Animal Science 71: 2860-2866.

Mahan, D. C and Newton, E. A., 1993. Journal of Animal Science 71: 3376-3382 Mathers, J. C and Annisonn E. F., 1993. Stoichiometry of polysaccharide fementation in the large intestine. In Dietary Fibre and Beyond—Australian Perspectives, volume 1, pp 123-135.

Martensson O, Biorklund M, Lambo M A, Duenas-Chasco M, Irastorza Am Holst O, Norin E, Welling G, Oste R, Onning G, Nutrition Research 25 (2005), 429-442.

Mathers, J. C. and Annison, E. F. 1993. Stoichiometry of polysaccharide fermentation in the large intestine. In: Dietary fibre and beyond—Australian perspectives, (ed. S, Samman and G. Annison) pp 123-125., Nutrition society of Australia occasional publications, Perth, Australia.

Mc Cracken, B. A, Spurlock, M. E., Roos, M. A., Zuckermann, F. A. and Gaskins, H. R., 1999. Journal of Nutrition 129: 613-619.

Melin, L., Mattisson, S., Katouli, M. and Wallgren, P., 2004. Journal of Veterinary Medicine B51:12-22.

Catherine Michel, Marc Lahaye, Christian Bonnett, Serge Mabeau And Jean-Luc Berry, 1996, British Journal of Nutrition, 75, 263-280

Miklkesen, L. L., Jensen, B. B., 1997. Effect of fructo-oligosaccharide (FO) on the intestinal microbiota of rats and determination of the fermentative transformation and energy transmission of FO. In: Hartemink, R. (Ed.), Proceedings of the International Symposium Non-digestible Oligosaccharides: Healthy food for the colon? 4-5 December, Wageningen, The Netherlands, p 158 (abstract).

Ministry of Agriculture, Fisheries and Food 1991. The Feedingstuffs Regulations 1991. Statutory instrument no. 2840, 9.76. Her Majesty's Stationary Office, London.

Mroz, Z., Moeser, A. J., Vreman, K., van Diepen, J. T. M., van Kempen, T., Canh, T. T., Jongbloed, A. W. 2000. Journal of Animal Science 78: 3096-3106.

Muller A, Ensley H, Pretus H, McNamee R, Jones E, McLaughlin E, Chandley W, Browder W, Lowman D and Williams D, Carbohydrate Research 299 (1997) 203-208.

Montagne, L., Pluske, J. R. and Hampson, D. J. 2003. Animal Feed Science and Technology 108: 95-117.

Mortensen, P. B., Hove, H., Clausen, M. R., Holtug, K., 1991 Scandanavian Journal of Gastroenterology December; 26 (12): 1285-1294.

Mul, A. J and Perry, F. G., 1994. In: Garnsworthy, P. C and Cole, D. J. A (eds). Recent Advances in Animal Nutrition 1994. Nottingham University Press, Nottingham, 57-79.

Muralidhara, K. S., G. G. Sheggeby, P. R. Elliker, D. C. England, and W. E. Sandine. 1977. Journal of FoodProtection 40:288-295.

Nahm, K. H. 2003 Critical Reviews in Environmental Science and Technology 30(2): 165-186.

Nessmith Jr, W. B., Nelssen, J. L., Tokach, M. D., Goodband, R. D and Bergstrom, J. R. 1997b. Journal of Animal Science 75: 3222-3228.

O'Doherty, J. V., Nolan, C. S, Callan, J. J and McCarthy, P., 2004. Animal Science 78: 419-428.

Onning, G., and Asp, N. G., 1995. British Journal of Nutrition 74: 229-237.

Owsley, W. F., Orr, D. E. and Tribble, L. F., 1986. Journal of Animal Science 63: 492-496.

Pacheco-Delayaye, E., 1995. Food Chemistry 65: 433-437.

Partridge, G. G and Gill, B. P., 1993. In: Wiseman, J and Garnsworthy, P. C. (eds) Recent Developments in Pig Nutrition 3. Nottingham University Press, Nottingham, UK, pp 205-237.

Pettersson A and Lindberg J E, Animal Feed Science Technology 66 (1997) 97-109.

Pettersson, D., and P. Aman. 1989. British journal of Nutrition. 62:139-149.

Pierce, Aileen, MsC Thesis (2002), 'The use of seaweed extract in animal nutrition' National University of Ireland, Dublin, University College Dublin, Ireland.

Pierce, K. M., Callan, J. J., Brophy, P. O., McCarthy, P., Sweeney, T., Fitzpatrick, E., Byrne, C., Ni Cheallaigh, S. and O'Doherty, J. V. 2004a. Journal of Animal Science 82, Supplement 1: 138-139

Pitcairn, C. E. R., Skiba, U. M., Sutton, M. A., Fowler, D., Munro, R. and Kennedy, V. 2002. Environmental Pollution 119: 9-21.

Pluske, J. R., Williams, I. H. and Aherne, F. A., 1995. Nutrition of the neonatal pig. In: M. A. Varley (ed.) The neonatal pigs: development and survival. CAB International, Wallinford, UK.

Pluske, J. R., Hampson, D. J and Williams I. H, 1997 Livestock Production Science 51:215-236.

Pluske, J. R., Kim, J. C., McDonald, D. E., Pethick, D. W. and Hampson, D. J. 2001. In: The weaner pig: Nutrition and Management. (ed. M. A. Varley and J. Wiseman) pp 81-111. CAB International, Wallingford, Oxon, UK.

Porter, M. G. and Murray, R. S., 2001. Grass and Forage Science 56: 405-411.

Read S, Currie G and Bacic A., Carbohydrate Research, 281 (1996) 187-210.

Riou, D., et al., Anticancer Research, vol. 16, pp. 1213-1218 (1996).

SAS. 1985. Statistical Analysis Systems. SAS Institute Inc., N.C., USA.

Sauer, W. C., Just, A., Jorgensen, H. H., Fekadu, M. and Eggum, B. O. 1980. Journal of Animal Science 69: 4070-4079.

Schmitz, W. 1995. In: Proceedings of the second European symposium on feed enzymes. (ed. W. van Hartingsveld, M. Hessing, J. P. van der Lugt and W. A. C. Somers) pp 95-101. TNO Nutrition and Food Research Institute, Zeist, The Netherlands.

S. Colliec et al Phytochemistry, 35, pp. 697-700, (1994).

Shibata, Hideyuld, et aiJ. Nutr. Sci. Vitaminol., vol. 45, pp. 325-336 (1999).

Smith, E. A. and MacFarlane, G. T. 1997. Anaerobe 3: 327-337.

Soergel, K. H., 1994. Clinical Investigations 72: 742-748.

Spreeuwenberg, M. A. M., Verdonk, J. M. A. J., Gaskins, J. H. and Verstegen, M. W. A. 2001. Journal of Nutrition 131:1520-1527.

Stanogias, G., and Pearce G. R. 1985. British Journal of Nutrition 53, 537-548 537 Statistics Analysis Systems Institute 1985. Stastical Analysis Systems version 6.12, SAS Institute Inc., Cary, N.C., USA.

Somogyi, M. 1960. Clinical Chemistry 6: 23-35.

Theander O, Westerlund E, Aman P & Graham H (1989) Animal Feed Science and Technology 23, 205.225.

Thomlinson, J. R. 1981. The Veterinary record 109: 120-122.

Tokach, M. D., Nelssen, J. L. and Allee, G. L., 1989. Journal of Animal Science 67: 1307-1312.

Turner, J. L., Dritz, J. J., Higgins and Minton, J. E., 2002. Journal of Animal Science 80: 1947-1953.

van Soest, P. J. 1976. Journal of the Association of Agricultural Chemists 46: 829-834.

Van Soest, P. J., Robertson, J. B. and Lewis, B. A. 1991. Journal of Dairy Science 74: 3583-3597.

Varel, V. H. 1987. Journal of Animal Science 65: 488-496.

Verstegen, M. W. and B. A. Williams, 2002. Journal of Animal Biotechnology 13: 113-127.

Wiliczkiewicz, A., Jamroz, D., Skorupinska, J., Orda, J., 1995. Wien. Tierarztl. Mschr. 82, 239_244.

Williams, C. H., David, D. J. and Iismaa, O., 1962. Journal of Animal Science 59: 381-385.

Williams, B. A., Martin, W. A., Verstegen and Tamminga S. 2001 Nutrition Research Reviews 14: 207-227.

Zijlstra, R. T., Whang, K-Y., Easter, R. A. and Odle, J., 1996. Journal of Animal Science 74: 2948-2959.

Zvyagintseva et al Carbohydrate research, 322, 32-29, 1999.

What is claimed is:

1. A method of treating animals or humans comprising: feeding the animals or humans a composition comprising: at least 8% w/w partially hydrolysed β-glucans, and at least 8% w/w partially hydrolysed α-fucans, in a synergistic amount to at least one of: increase growth of beneficial microbes, reduce levels of harmful microbes selected from *E. coli* or *Salmonella* in animal or human intestines, improve gut structure, reduce gut inflammation, improved nutrient digestibility, improve mineral absorption, improve growth performance, or reduce gut infection and inflammation.

2. The method of claim 1, wherein the β-glucans comprise at least 8% w/w.

3. The method of claim 1, wherein the α-fucans comprise at least 8% w/w.

4. The method of claim 1, wherein the β-glucans comprise β-(1, 3)(1, 6)-glucans.

5. The method of claim 1, wherein the β-glucans or the α-fucans are derived from a seaweed.

6. The method of claim 5, wherein the seaweed is selected from *Laminariaceae, Fucaceae* and *Gigartinaceae, Ascophyllum, Laminaria, Durvillea, Macrocystis, Chondrus, Ecklonia* or any combinations thereof.

7. The method of claim 1, wherein the β-glucans comprise laminarin.

8. The method of claim 1, wherein the α-fucans comprise fucoidan.

9. The method of claim 1, further comprises mannitol, lactose or combinations thereof.

10. The method of claim 1, wherein the β-glucans or α-fucans are derived from seaweed by acid-extraction.

11. The method of claim 1, further comprising hydrolyzing the composition with one or more acids selected from lactic acid, hydrochloric acid, sulfuric acid, citric acid, propionic acid, or any combinations thereof.

12. The method of claim 1, wherein the composition is in a powder form or a liquid form.

13. The method of claim 1, wherein the composition further comprises one or more probiotic cultures.

14. The method of claim 13, wherein the one or more probiotic cultures are selected from *Bifidobacteria* or *Lactobacillus*.

15. The method of claim 13, wherein the one or more probiotic cultures is selected from the group consisting of *Bifidobacterium adolescentis, Lactobacillus leichmannii, Lactobacillus plantarum, Lactobacillus cellobiosius, Lactobacillus acidophilus*, and any combinations thereof.

16. The method of claim 1, wherein the composition is mixed with one or more probiotic cultures to form a tablet, or capsule.

17. The method of claim 1, wherein the composition comprises a synergistic amount of β-glucans and α-fucans.

18. The method of claim 1, wherein the β-glucans comprise an amount between 8% and 30% by weight.

19. The method of claim 1, wherein the α-fucans comprise an amount between 8% and 30% by weight.

20. The method of claim 1, wherein the composition consists essentially of 8% to 30% w/w partially acid treated β-glucans, and 8% to 30% w/w partially acid treated α-fucans in a synergistic amount that at least one of: promotes the growth of beneficial microbes, reduces the levels of harmful microbes selected from *E. coli* or *Salmonella* in animal or human intestines, improves gut structure, reduces gut inflammation, increases nutrient digestibility, increases mineral absorption, increases growth performance in animals or humans, or reduces in-feed antibiotics and treatment for gut infection and inflammation, wherein the composition is formulated for oral delivery.

* * * * *